US008138219B2

(12) United States Patent
Pasternak et al.

(10) Patent No.: US 8,138,219 B2
(45) Date of Patent: Mar. 20, 2012

(54) TRYPTAMINE SULFONAMIDES AS 5-HT$_6$ ANTAGONISTS

(75) Inventors: Alexander Pasternak, Princeton, NJ (US); Michael J. Szymonifka, Clark, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 63 days.

(21) Appl. No.: 12/739,984

(22) PCT Filed: Nov. 25, 2008

(86) PCT No.: PCT/US2008/013104
§ 371 (c)(1),
(2), (4) Date: Apr. 27, 2010

(87) PCT Pub. No.: WO2009/073118
PCT Pub. Date: Jun. 11, 2009

(65) Prior Publication Data
US 2010/0256106 A1 Oct. 7, 2010

Related U.S. Application Data

(60) Provisional application No. 61/005,288, filed on Dec. 4, 2007.

(51) Int. Cl.
*A61K 31/404* (2006.01)
*C07D 209/14* (2006.01)
(52) U.S. Cl. .................. 514/415; 548/506
(58) Field of Classification Search .............. 548/506
See application file for complete search history.

(56) References Cited

U.S. PATENT DOCUMENTS

| 7,022,701 B2 | 4/2006 | Cole et al. |
| 2003/0171353 A1 | 9/2003 | Cole et al. |

FOREIGN PATENT DOCUMENTS

| EP | 1510208 | 3/2005 |
| FR | 2 181 559 A1 | 12/1973 |
| WO | 00/34242 | 6/2000 |
| WO | 02/078693 | 10/2002 |
| WO | 2006/126939 | 11/2006 |

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Aug. 23, 2003]. Retrieved from the Internet, URL; http://www.cnn.com/2003/Health/conditions/O9/24/alzheimers.drug.ap/indexhtml>.*
Boch, et al. Document No. 80:108368 retrieved from CAPLUS (1973).*
Holenz, "Medicinal chemistry strategies to 5-HT6 receptor ligands . . . ", Drug Discovery Today (2006), vol. 11, pp. 283-299.
Zhang, "Effects of mutations at conserved TM II residues . . . ", Eur. J. Pharmacology (2006), vol. 534, pp. 77-82.
Bentley, "Investigation of stretching behaviour induced by the selective 5-HT6 . . . ", Brit. J. of Pharmacology (1999), vol. 126, pp. 1537-1542.
Bourson, "Involvement of 5-HT6 receptors in nigro-striatal . . . ", Brit. J. of Pharmacology (1998), vol. 125, pp. 1562-1566.
Dawson, "The 5-HT6 receptor antagonist SB-271046 . . . ", Neuropsychopharmacology (2001), vol. 25, pp. 662-668.
Foley, "The 5-HT6 receptor antagonist SB-271046 reverses . . . ", Neuropsychopharmacology (2004), vol. 29, pp. 93-100.
Gerard, "Immuno-localization of serotonin 5-HT6 receptor-like . . . ", Brain Research (1997), vol. 746, pp. 207-219.
Hatcher, "5-HT6 receptor antagonists improve performance . . . ", Psychopharmacology (2005), vol. 181, pp. 253-259.
Kohen, "Cloning, characterization, and chromosomal localization . . . ", J. of Neurochemistry (1996), vol. 66, pp. 47-26.
Lacroix, "5-HT6 receptor antagonist SB-271046 enhances . . . ", Synapse (2004), vol. 51, pp. 158-164.
Roth, "Binding of typical and atypical antipsychotic agents . . . ", J. Pharmacol. and Experim. Therap. (1994), vol. 268, pp. 1403-1410.
Stean, "Anticonvulsant properties of the selective 5-HT6 receptor . . . ", Brit. J. of Pharmacology, (1999), vol. 127, Proc. Supp. 131P.
Yoshioka, "Central distribution and function of 5-HT6 receptor . . . ", Life Sciences (1998), vol. 62, pp. 1473-1477.
Woolley, "Reversal of a cholinergic-induced deficit . . . ", Psychopharmacology (2003), vol. 170, pp. 358-367.
Woolley, "A role for 5-ht6 receptors in retention . . . ", Neuropharmacology (2001), vol. 41, pp. 210-219.
Ward, "Localization of serotonin subtype 6 receptor . . . ", Neuroscience (1995), vol. 64, pp. 1105-1111.
Sleight, "The 5-hydroxytryptamine6 receptor . . . ", Exp. Opin. Thor. Patents (1998), vol. 8, pp. 1217-1224.
Sleight, "Characterization of Ro 04-6790 and Ro 63-0563: . . . ", Brit. J. of Pharmacology (1998), vol. 124, pp. 556-562.
Slassi, "Recent progress in 5-HT6 receptor antagonists . . . ", Exp. Opin. Thor. Patents (2002), vol. 12, pp. 513-527.
Schechter, "Innovative approaches for the development of antidepressant . . . ", NeuroRx (2005), vol. 2, pp. 590-611.
Riemer, "Influence of the 5-HT6 receptor on acetylcholine . . . ", J. Med. Chem. (2003), vol. 46, pp. 1273-1276.
NPL-PCT/US2008/013104—Int'l Preliminary Report on Patentability, dated Jun. 8, 2010.

* cited by examiner

*Primary Examiner* — Shawquia Young
(74) *Attorney, Agent, or Firm* — Baerbel R. Brown; John C. Todaro

(57) ABSTRACT

Novel compounds of the structural formula (I) are antagonists of the 5-HT$_6$ receptor and are useful in the treatment, prevention and suppression of diseases mediated by the 5-HT$_6$ receptor. The compounds of the present invention are useful in the treatment of obesity, diabetes, metabolic disorder, cognitive disorders, age related cognitive disorder, depression, mania, bipolar disorders, schizophrenia, anxiety, generalized anxiety disorder, panic disorder, and obsessive compulsive disorder, epilepsy, convulsions, migraine, substance withdrawal from substances including but not limited to opiates, nicotine, tobacco products, alcohol, benzodiazepines, sedatives, and the like, sleep disorders, attention deficit/hyperactivity disorder, and Alzheimer's disease.

15 Claims, No Drawings

TRYPTAMINE SULFONAMIDES AS 5-HT$_6$ ANTAGONISTS

CROSS-REFERENCE TO RELATED APPLICATIONS

This application is a U.S. National Phase application under 35 U.S.C. §371 of PCT Application No. PCT/US2008/013104, filed Nov. 25, 2008, which claims priority from and the benefit of U.S. Provisional Application No. 61/005,288, filed Dec. 4, 2007.

BACKGROUND OF THE INVENTION

Serotonin (5-hydroxy-tryptamine) (5-HT) receptors play an important role in many physiological and pathological functions like anxiety, sleep regulation, aggression, feeding and depression. The 5-HT receptors are distributed throughout the body and can be divided is into seven different 5-HT receptor subtypes, i.e. 5-HT$_1$, 5-HT$_2$, 5-HT$_3$, 5-HT$_4$, 5-HT$_5$, 5-HT$_6$ and 5-HT$_7$, with different properties. The 5-HT$_6$ receptor is mostly found in the central nervous system (CNS). From in situ hybridization studies it is known that the 5-HT$_6$ receptor in rat brain is localized in areas like striatum, nucleus accumbens, olfactory tubercle and hippocampal formation (Ward et al., Neuroscience, 64, p 1105-1111, 1995).

Scientific research has revealed a potential therapeutic use for modulators of the 5-HT$_6$ receptor, especially with regard to various CNS disorders. Blocking 5-HT$_6$ receptor function has been shown to enhance cholinergic transmission (Bentley et al, Br J Pharmacol 126: 1537-1542, 1999; Riemer et al J Med Chem 46, 1273-1276). 5-HT$_6$ antagonist have also been shown to reverse cognitive deficits in in vivo cognition models induced by the muscarinic antagonist scopolamine (Woolley et al. Phychopharmacolgy, 170, 358-367, 2003; Foley et al. Neuropsychopharmacology, 29 93-100, 2004). Studies have shown that 5-HT$_6$ antagonists increase levels of glutamate and aspartate in the frontal cortex and dorsal hippocampus as well as acetylcholine in the frontal cortex. These neurochemicals are known to be involved in memory and cognition (Dawson et al., Neuropsychopharmacology, 25(5), p 662-668, 2001; Gerard et al., Brain Res., 746, p 207-219, 1997; and Riemer et al J Med Chem 46(7), p 1273-1276, 2003).

Acetylcholinesterase inhibitors increase the levels of acetylcholine in the CNS and are used in the treatment of cognitive disorders such as Alzheimer's disease. 5-HT$_6$ antagonists may therefore also be used in the treatment of cognitive disorders (Bentley et al., Br. J. Pharmacol. (1999) 126, 1537-1542).

Studies have also shown that 5-HT$_6$ antagonists increase the level of dopamine and noradrenaline in the medial prefrontal cortex (Lacroix et al. Synapse 51, 158-164, 2004). In addition, 5-HT$_6$ receptor antagonists have been shown to improve performance in the attentional set shifting task (Hatcher et al. Psychopharmacology 181 (2):253-9, 2005). Therefore, 5-HT$_6$ ligands are expected to be useful in the treatment of disorders where cognitive deficits are a feature, such as schizophrenia. Several antidepressants and atypical antipsychotics bind to the 5-HT$_6$ receptor and this may be a factor in their profile of activities (Roth et al., J. Pharm. Exp. Therapeut., 268, 1402-1420, 1994; Sleight et al., Exp. Opin. Ther. Patents, 8, 1217-1224, 1998; Kohen et al., J. Neurochem., 66(1), p 47-56, 1996; Sleight et al. Brit. J. Pharmacol., 124, p 556-562, 1998; and Bourson et al., Brit. J. Pharmacol., 125, p 1562-1566, 1998).

Studies have described the potential use of 5-HT$_6$ modulators in the treatment of epilepsy (Stean et al., Brit. J. Pharmacol. 127 Proc. Supplement 131P, 1999). 5-HT$_6$ receptors have also been linked to generalized stress and anxiety states (Yoshioka et al., Life Sciences, 62, 17/18, p 1473-1477, 1998). 5-HT$_6$ agonists have been shown to elevate levels of GABA in brain regions associated with anxiety and shown positive effects in models predictive of obsessive-compulsive disorder (Schechter et al. NeuroRx. 2005 October; 2(4): 590-611). The use of modulators for this receptor is therefore expected for a wide range of CNS disorders.

Moreover, a reduction in food intake in rats has been reported using 5-HT$_6$ receptor modulators (Woolley et al. Neuropharmacology 41 (2001) 210-219; Chen et al., European J. Pharmacology 534 (2006) 77-82). 5-HT$_6$ receptor modulators, such as 5-HT$_6$ antagonists, may therefore also be useful in the treatment of feeding disorders like anorexia, obesity, bulimia and similar disorders, including but not limited to, type 2 diabetes.

Indole 5-HT$_6$ antagonists are disclosed in WO 02/078693.

SUMMARY OF THE INVENTION

The present invention is concerned with novel indoles of structural Formula I:

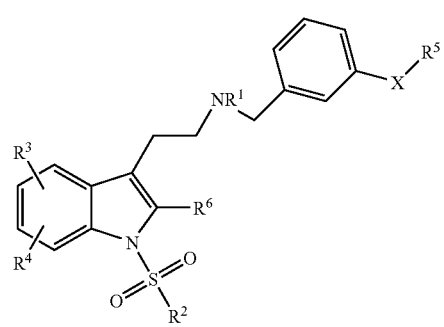

and pharmaceutically acceptable salts thereof which are modulators of and, in particular, antagonists of the 5-HT$_6$ receptor and are useful in the treatment, prevention or suppression of diseases mediated by the 5-HT$_6$ receptor. In one aspect, the invention is concerned with the use of these novel compounds to selectively antagonize the 5-HT$_6$ receptor. As such, compounds of the present invention are useful in the treatment of obesity, diabetes, metabolic disorder, cognitive disorders, age related cognitive disorder, depression, mania, bipolar disorders, schizophrenia, anxiety, generalized anxiety disorder, panic disorder, and obsessive compulsive disorder, epilepsy, convulsions, migraine, substance withdrawal from substances including but not limited to opiates, nicotine, tobacco products, alcohol, benzodiazepines, sedatives, and the like, sleep disorders, attention deficit/hyperactivity disorder, and Alzheimer's disease.

The present invention is also concerned with treatment of these conditions, and the use of compounds of the present invention for manufacture of a medicament useful in treating these conditions. The present invention is also concerned with treatment of these conditions through a combination of compounds of formula I and other currently available pharmaceuticals.

The invention is also concerned with pharmaceutical formulations comprising one of the compounds as an active ingredient, as well as processes for preparing the compounds of this invention.

DETAILED DESCRIPTION OF THE INVENTION

The compounds of the present invention are represented by the compound of structural formula I:

I or a pharmaceutically acceptable salt thereof, wherein:
X is selected from the group consisting of:
(1) —O—,
(2) —NH—,
(3) —S—,
(4) —SO$_2$—,
(5) —CH$_2$—,
(6) —CHF—,
(7) —CF$_2$—,
(8) —CH(OH)—,
(9) —CO—,
(10) —NHCO—,
(11) —CONH—, and
(12) —CO$_2$—;
R$^1$ is selected from the group consisting of:
(1) hydrogen, and
(2) —C$_{1-3}$alkyl;
R$^2$ is selected from the group consisting of:
(1) —C$_{1-6}$alkyl,
(2) —C$_{3-7}$cycloalkyl,
(3) —C$_{2-6}$cycloheteroalkyl,
(4) phenyl,
(5) naphthyl, and
(6) heteroaryl,
wherein each alkyl, cycloalkyl, cycloheteroalkyl, phenyl, naphthyl and heteroaryl is unsubstituted or substituted with 1, 2 or 3 substituents selected from —C$_{1-6}$alkyl, —C$_{3-7}$cycloalkyl, halogen, —CF$_3$, —OCF$_3$, —CN, —SO$_2$R$^7$, —CO$_2$R$^8$, phenyl, —C$_{2-6}$cycloheteroalkyl, —OR$^7$, —SR$^7$, —CONHR$^8$, —NHSO$_2$R$^7$, and —NHCOR$^7$;
R$^3$ and R$^4$ are independently selected from the group consisting of:
(1) hydrogen,
(2) halogen,
(3) —C$_{1-6}$alkyl,
(4) —OC$_{1-6}$alkyl,
(5) —CN,
(6) —OR$^7$,
(7) —SO$_2$R$^7$,
(8) —SR$^7$,
(9) —N(R$^8$)$_2$,
(10) —CONHR$^8$,
(11) —NHSO$_2$R$^7$, and
(12) —NHCOR$^7$,
wherein each alkyl is unsubstituted or substituted on each carbon with 1, 2 or 3 substituents selected from halogen, —C$_{1-6}$alkyl, —C$_{3-7}$cycloalkyl, —CF$_3$, —OCF$_3$, —CN, —SO$_2$R$^7$, —CO$_2$R$^8$, phenyl, —C$_{2-6}$cycloheteroalkyl, —O$^7$, —SR$^7$, —CONHR$^8$, —NHSO$_2$R$^7$, and —NHCOR$^7$;
R$^5$ is selected from:
(1) —C$_{1-6}$alkyl,
(2) —C$_{1-6}$alkenyl,
(3) phenyl, and
(4) benzyl,
wherein each alkyl, alkenyl, phenyl and benzyl are unsubstituted or substituted on each carbon with 1, 2 or 3 substituents selected from: halogen, C$_{1-6}$alkyl, C$_{3-7}$cycloalkyl, —CF$_3$, —OCF$_3$, —CN, —SO$_2$R$^7$, —CO$_2$R$^8$, phenyl, —C$_2$-C$_6$cycloheteroalkyl, —OR$^7$, —SR$^7$, —CONHR$^8$, —NHSO$_2$R$^7$, and —NHCOR$^7$;
R$^6$ is selected from the group consisting of:
(1) hydrogen, and
(2) —C$_{1-4}$alkyl;
R$^7$ is selected from a group consisting of:
(1) —C$_{1-6}$alkyl, and
(2) —C$_{3-6}$cycloalkyl; and
R$^8$ is selected from a group consisting of:
(1) hydrogen,
(2) —C$_{1-6}$alkyl, and
(3) —C$_{3-6}$cycloalkyl.

In one embodiment of the present invention, X is selected from the group consisting of: —O—, —NH—, —S—, —SO$_2$—, —CH$_2$—, —CHF—, —CF$_2$—, —CH(OH)—, —CO—, —NHCO—, —CONH— and —CO$_2$—.

In another embodiment of the present invention, X is selected from the group consisting of: —O—, —NH—, —S—, —SO$_2$—, —CH$_2$—, —CHF—, —CH(OH)— and —CO—.

In another embodiment of the present invention, X is selected from the group consisting of: —O—, —NH—, —S—, and —CH$_2$—. In a class of this embodiment, X is —O—. In another class of this embodiment, X is —S—.

In another embodiment of the present invention, R$^1$ is hydrogen.

In another embodiment of the present invention, R$^2$ is selected from the group consisting of: —C$_1$-C$_6$alkyl, —C$_3$-C$_7$cycloalkyl, -phenyl, -naphthyl, heteroaryl and —C$_2$-C$_6$cycloheteroalkyl, wherein each alkyl, cycloalkyl, phenyl, naphthyl, heteroaryl and cycloheteroalkyl is unsubstituted or substituted with 1, 2 or 3 substituents selected from C$_1$-C$_6$alkyl, C$_3$-C$_7$cycloalkyl, halogen, CF$_3$, OCF$_3$, CN, SO$_2$R$^7$, CO$_2$R$^8$, phenyl, —C$_2$-C$_6$cycloheteroalkyl, —OR$^7$, SR$^7$, CONHR$^8$, NHSO$_2$R$^7$, and NHCOR$^7$. In a class of this embodiment, R$^2$ is selected from: —C$_1$-C$_6$alkyl and phenyl, wherein each alkyl and phenyl is unsubstituted or substituted with 1, 2 or 3 substituents selected from C$_1$-C$_6$alkyl, C$_3$-C$_7$cycloalkyl, halogen, CF$_3$, OCF$_3$, CN, SO$_2$R$^7$, CO$_2$R$^8$, phenyl, cycloheteroalkyl, —OR$^7$, SR$^7$, CONHR$^8$, NHSO$_2$R$^7$, and NHCOR$^7$. In another class of this embodiment, R$^2$ is selected from: —C$_1$-C$_6$alkyl and phenyl, wherein each alkyl and phenyl is unsubstituted or substituted with 1, 2 or 3 substituents selected from C$_1$-C$_6$alkyl, C$_3$-C$_7$cycloalkyl, halogen, CF$_3$, OCF$_3$, CN, SO$_2$R$^7$, CO$_2$R$^8$, phenyl, —OR$^7$, SR$^7$, CONHR$^8$, NHSO$_2$R$^7$, and NHCOR$^7$. In another class of this embodiment, R$^2$ is selected from: —C$_1$-C$_6$alkyl and phenyl, wherein each alkyl and phenyl is unsubstituted or substituted with 1, 2 or 3 substituents selected from C$_1$-C$_6$alkyl, C$_3$-C$_7$cycloalkyl, halogen, CF$_3$, OCF$_3$, CN, SO$_2$R$^7$, CO$_2$R$^8$, —OR$^7$, SR$^7$, CONHR$^8$, NHSO$_2$R$^7$, and NHCOR$^7$. In another class of this embodiment, R$^2$ is selected from: methyl, ethyl, isopropyl, and phenyl, wherein each phenyl is unsubstituted or substituted with 1, 2 or 3 substituents selected from: halogen, CF$_3$, OCF$_3$ and —OR$^7$. In a subclass of this class, R$^2$ is selected from: methyl, ethyl, isopropyl, and phenyl, wherein phenyl is unsubstituted or substituted with 1, 2 or 3 substituents selected from halogen CF$_3$, OCF$_3$ and —OCH$_3$. In another subclass of this class, R$^2$ is selected from: methyl, and phenyl, wherein phenyl is unsubstituted or substituted with 1, 2 or 3 substituents selected from halogen CF$_3$, OCF$_3$ and —OCH$_3$.

In another embodiment of the present invention, R$^2$ is selected from: methyl, ethyl, isopropyl, and phenyl, wherein each methyl, ethyl, isopropyl and phenyl is unsubstituted or substituted with 1, 2 or 3 substituents selected from C$_1$-C$_6$alkyl, C$_3$-C$_7$cycloalkyl, halogen, CF$_3$, OCF$_3$, CN, SO$_2$R$^7$, CO$_2$R$^8$, phenyl, —C$_{2-6}$cycloheteroalkyl, —OR$^7$, SR$^7$, CONHR$^8$, NHSO$_2$R$^7$, and NHCOR$^7$. In a class of this embodiment, R$^2$ is selected from: methyl, ethyl, isopropyl, and phenyl, wherein each methyl, ethyl, isopropyl and phenyl is unsubstituted or substituted with 1, 2 or 3 substituents selected from: C$_1$-C$_6$alkyl, C$_3$-C$_7$cycloalkyl, halogen, CF$_3$, OCF$_3$, CN, SO$_2$R$^7$, CO$_2$R$^8$, phenyl, —OR$^7$, SR$^7$, CONHR$^8$, NHSO$_2$R$^7$, and NHCOR$^7$. In another class of this embodiment, R$^2$ is selected from: —C$_1$-C$_6$alkyl, methyl, ethyl, isopropyl, and phenyl, wherein each alkyl and phenyl is unsubstituted or substituted with 1, 2 or 3 substituents selected from C$_1$-C$_6$alkyl, C$_3$-C$_7$cycloalkyl, halogen, CF$_3$, OCF$_3$, CN, SO$_2$R$^7$, CO$_2$R$^8$, —OR$^7$, SR$^7$, CONHR$^8$, NHSO$_2$R$^7$, and NHCOR$^7$. In another class of this embodiment, R$^2$ is selected from: methyl, ethyl, isopropyl, and phenyl, wherein each ethyl, methyl, isopropyl and phenyl is unsubstituted or substituted with 1, 2 or 3 substituents selected from C$_1$-C$_6$alkyl, C$_3$-C$_7$cycloalkyl, halogen, CF$_3$, OCF$_3$, CN, SO$_2$R$^7$, CO$_2$R$^8$, —OR$^7$, SR$^7$, CONHR$^8$, NHSO$_2$R$^7$, and NHCOR$^7$. In another class of this embodiment, R$^2$ is selected from: methyl, ethyl, isopropyl, and phenyl, wherein each phenyl is unsubstituted or substituted with 1, 2 or 3 substituents selected from: halogen, CF$_3$, OCF$_3$ and —OR$^7$. In a subclass of this class, R$^2$ is selected from: methyl, ethyl, isopropyl, and phenyl, wherein each phenyl is unsubstituted or substituted with 1, 2 or 3 substituents selected from halogen CF$_3$, OCF$_3$ and —OCH$_3$. In another subclass of this class, R$^2$ is selected from: methyl, and phenyl, wherein each phenyl is unsubstituted or substituted with 1, 2 or 3 substituents selected from halogen CF$_3$, OCF$_3$ and —OCH$_3$.

In another embodiment of the present invention, R$^3$ and R$^4$ are independently selected from the group consisting of: hydrogen, halogen, —C$_{1-6}$alkyl, —OC$_{1-6}$alkyl, —CN, —OR$^7$, —SO$_2$R$^7$, —SR$^7$, —N(R$^8$)$_2$, —CONHR$^8$, —NHSO$_2$R$^7$, and —NHCOR$^7$, wherein each —C$_{1-6}$alkyl and —OC$_{1-6}$alkyl is unsubstituted or substituted on each carbon with 1, 2 or 3 substituents selected from halogen, and C$_1$-C$_6$alkyl, C$_3$-C$_7$cycloalkyl, CF$_3$, OCF$_3$, CN, SO$_2$R$^7$, CO$_2$R$^8$, phenyl, —C$_2$-C$_6$cycloheteroalkyl, —OR$^7$, SR$^7$, CONHR$^8$, NHSO$_2$R$^7$, and NHCOR$^7$.

In another embodiment of the present invention, R$^3$ and R$^4$ are independently selected from the group consisting of: hydrogen, halogen, —C$_{1-6}$alkyl, —OC$_{1-6}$alkyl, —CN, —SO$_2$R$^7$, —SR$^7$, —N(R$^8$)$_2$, —CONHR$^8$, —NHSO$_2$R$^7$, and —NHCOR$^7$, wherein each —C$_{1-6}$alkyl and —OC$_{1-6}$alkyl is unsubstituted or substituted on each carbon with 1, 2 or 3 substituents selected from halogen. In a class of this embodiment, R$^3$ and R$^4$ are independently selected from the group consisting of: hydrogen, halogen, —C$_{1-6}$alkyl, —OC$_{1-6}$alkyl, —CN, —OR$^7$, —SO$_2$R$^7$, —SR$^7$, —N(R$^8$)$_2$, —CONHR$^8$, —NHSO$_2$R$^7$, and —NHCOR$^7$, wherein each —C$_{1-6}$alkyl and —OC$_{1-6}$alkyl is unsubstituted or substituted on each carbon with 1, 2 or 3 substituents selected from fluorine.

In another embodiment of the present invention, R$^3$ and R$^4$ are independently selected from the group consisting of: hydrogen, halogen, —C$_{1-6}$alkyl, —OC$_{1-6}$alkyl, —CN, —SO$_2$R$^7$, and —SR$^7$, wherein each —C$_{1-6}$alkyl and —OC$_{1-6}$ alkyl is unsubstituted or substituted on each carbon with 1, 2 or 3 substituents selected from halogen, and C$_1$-C$_6$alkyl, C$_3$-C$_7$cycloalkyl, CF$_3$, OCF$_3$, CN, SO$_2$R$^7$, CO$_2$R$^8$, phenyl, —C$_2$-C$_6$cycloheteroalkyl, SR$^7$, CONHR$^8$, NHSO$_2$R$^7$, and NHCOR$^7$. In a subclass of this embodiment, R$^3$ and R$^4$ are independently selected from the group consisting of: hydrogen, halogen, —C$_{1-6}$alkyl, —OC$_{1-6}$alkyl, —CN, —SO$_2$R$^7$, and —SR$^7$, wherein each —C$_{1-6}$alkyl and —OC$_{1-6}$alkyl is unsubstituted or substituted on each carbon with 1, 2 or 3 substituents selected from halogen. In another subclass of this embodiment, R$^3$ and R$^4$ are independently selected from the group consisting of: hydrogen, halogen, —C$_{1-6}$alkyl, —OC$_{1-6}$ alkyl, —CN, —SO$_2$R$^7$, and —SR$^7$, wherein each —C$_{1-6}$alkyl and —OC$_{1-6}$alkyl is unsubstituted or substituted on each carbon with 1, 2 or 3 substituents selected from fluorine.

In another embodiment of the present invention, R$^3$ is selected from: -hydrogen, -halogen, —C$_{1-6}$alkyl, —OC$_{1-6}$ alkyl, —CN, —SO$_2$R$^7$, and —SR$^7$; wherein each —C$_{1-6}$alkyl and —OC$_{1-6}$alkyl is unsubstituted or substituted on each carbon with 1, 2 or 3 substituents selected from fluoro. In another embodiment of the present invention, R$^3$ is selected from: -hydrogen, fluorine, chlorine, bromine, —CF$_3$, —OCF$_3$, —CN, —SO$_2$R$^7$, and —SR$^7$. In a class of this embodiment, R$^3$ is selected from: hydrogen and halogen. In a subclass of this class, R$^3$ is selected from: hydrogen, fluoro, and chloro. In another class of this embodiment, R$^3$ is selected from: hydrogen and fluorine. In another class of this embodiment, R$^3$ is -hydrogen. In yet another class of this embodiment, R$^3$ is fluorine.

In another embodiment of the present invention, R$^4$ is selected from: -hydrogen, -fluoro, -chloro, -bromo, —CF$_3$, —OCF$_3$, —CN, —SO$_2$R$^7$, and —SR$^7$. In a class of this embodiment, R$^4$ is selected from: hydrogen and halogen. In a subclass of this class, R$^4$ is selected from: hydrogen, fluorine, and chlorine. In another class of this embodiment, R$^4$ is hydrogen.

In another embodiment of the present invention, R$^5$ is selected from: —C$_{1-6}$alkyl, —C$_{1-6}$alkenyl, phenyl, and benzyl, wherein each alkyl, alkenyl, phenyl and benzyl is unsubstituted or substituted on each carbon with 1, 2 or 3 substituents selected from: halogen, C$_{1-6}$alkyl, C$_{3-7}$cycloalkyl, —CF$_3$, —OCF$_3$, —CN, —SO$_2$R$^7$, —CO$_2$R$^8$, phenyl, —C$_{2-6}$cycloheteroalkyl, —OR$^7$, —SR$^7$, —CONHR$^8$, —NHSO$_2$R$^7$, and —NHCOR$^7$. In a class of this embodiment, R$^5$ is selected from: —C$_{1-6}$alkyl, —C$_{1-6}$alkenyl, phenyl, and benzyl, wherein each alkyl, alkenyl, phenyl and benzyl is unsubstituted or substituted on each carbon with 1, 2 or 3 substituents selected from halogen. In another class of this embodiment, R$^5$ is selected from: —C$_{1-6}$alkyl, —C$_{1-6}$alkenyl, phenyl, and benzyl, wherein each alkyl, alkenyl, phenyl and benzyl is unsubstituted or substituted on each carbon with 1, 2 or 3 substituents selected from fluorine. In another class of this embodiment, R$^5$ is —C$_{1-6}$alkyl, wherein each alkyl is unsubstituted or substituted on each carbon with 1, 2 or 3 substituents selected from halogen, —C$_{1-6}$alkyl, —C$_{3-7}$cycloalkyl, —CF$_3$, —OCF$_3$, —CN, —SO$_2$R$^7$, —CO$_2$R$^8$, phenyl, —C$_{2-6}$cycloheteroalkyl, —OR$^7$, —SR$^7$, —CONHR$^8$, —NHSO$_2$R$^7$, and —NHCOR$^7$. In another class of this embodiment, R$^5$ is —C$_{1-6}$alkyl, wherein each alkyl is unsubstituted or substituted on each carbon with 1, 2 or 3 substituents selected from halogen. In a subclass of this class, $R^5$ is —$C_{1-6}$alkyl, wherein each alkyl carbon is unsubstituted or substituted on each carbon with 1, 2 or 3 substituents selected from fluoro. In another subclass of this class, $R^5$ is fluorinated $C_{2-4}$ alkyl. In another subclass of this class, $R^5$ is —$CH_2CF_2CHF_2$.

In yet another embodiment of the present invention, $R^5$ is selected from: —$C_{1-6}$alkyl, —$C_{1-6}$alkenyl, phenyl, and benzyl, wherein each alkyl, alkenyl, phenyl and benzyl is unsubstituted or substituted on each carbon with 1, 2 or 3 substituents selected from: halogen, —$CF_3$, —$OCF_3$, —$OR^7$, and —$SR^7$, —$CONHR^8$, —$NHSO_2R^7$.

In another embodiment of the present invention, $R^6$ is selected from: hydrogen and —$C_1$-$C_4$alkyl. In a class of this embodiment, $R^6$ is hydrogen.

In one embodiment of the present invention, $R^7$ is selected from: —$C_1$-$C_6$alkyl, and —$C_3$-$C_6$cycloalkyl. In a class of this embodiment, $R^7$ is —$C_1$-$C_6$alkyl. In a subclass of this class, $R^7$ is methyl.

In another embodiment of the present invention, $R^8$ is selected from: hydrogen, —$C_1$-$C_6$alkyl, and —$C_3$-$C_6$cycloalkyl.

In another embodiment of the present invention, the invention relates to the compound of structural formula I, or a pharmaceutically acceptable salt thereof, wherein:
X is —O—;
$R^1$ is hydrogen;
$R^2$ is selected from:
 (1) methyl,
 (2) ethyl,
 (3) isopropyl, and
 (4) phenyl,
wherein phenyl is unsubstituted or substituted with 1, 2 or 3 substituents selected from halogen, —$CF_3$, —$OCF_3$ and —$OCH_3$;
$R^3$ is selected from the group consisting of:
 (1) hydrogen,
 (2) fluoro,
 (3) chloro,
 (4) bromo,
 (5) —$CF_3$,
 (6) —$OCF_3$,
 (7) —CN,
 (8) —$OR^7$,
 (9) —$SO_2R^7$, and
 (10) —$SR^7$;
$R^4$ is selected from the group consisting of:
 (1) hydrogen,
 (2) fluoro, and
 (3) chloro;
$R^5$ is $C_2$-$C_4$ alkyl, wherein each alkyl carbon is unsubstituted or substituted with 1, 2 or 3 fluoro substituents;
$R^6$ is hydrogen;
$R^7$ is selected from a group consisting of:
 (1) —$C_{1-6}$alkyl, and
 (2) —$C_{3-6}$cycloalkyl; and
$R^8$ is selected from a group consisting of:
 (1) hydrogen,
 (2) —$C_{1-6}$alkyl, and
 (3) —$C_{3-6}$cycloalkyl.

In another embodiment of the present invention, the invention relates to the compound of structural formula IA:

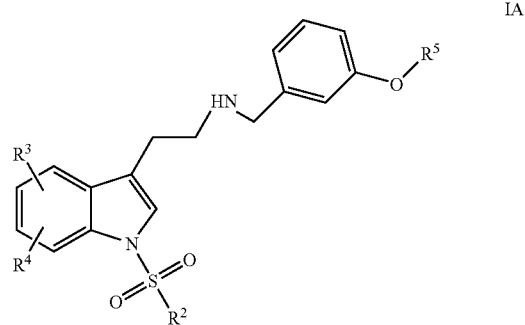

or a pharmaceutically acceptable salt thereof, wherein:
$R^2$ is selected from:
 (1) methyl,
 (2) ethyl,
 (3) isopropyl, and
 (4) phenyl,
wherein phenyl is unsubstituted or substituted with 1, 2 or 3 substituents selected from halogen, —$CF_3$, —$OCF_3$ and —$OCH_3$;
$R^3$ is selected from the group consisting of:
 (1) hydrogen,
 (2) fluoro,
 (3) chloro,
 (4) bromo,
 (5) —$CF_3$,
 (6) —$OCF_3$,
 (7) —CN,
 (8) —$OR^7$,
 (9) —$SO_2R^7$, and
 (10) —$SR^7$;
$R^4$ is selected from the group consisting of:
 (1) hydrogen,
 (2) fluoro, and
 (3) chloro;
$R^5$ is $C_2$-$C_4$ alkyl, wherein each alkyl carbon is unsubstituted or substituted with 1, 2 or 3 fluoro substituents; and
$R^7$ is selected from a group consisting of:
 (1) —$C_{1-6}$alkyl, and
 (2) —$C_{3-6}$cycloalkyl.

In another embodiment of the present invention, the invention relates to the compound of structural formula IB:

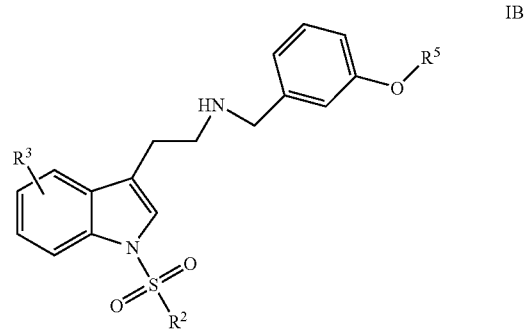

or a pharmaceutically acceptable salt thereof, wherein:
R² is selected from:
(1) methyl,
(2) ethyl,
(3) isopropyl, and
(4) phenyl,
wherein phenyl is unsubstituted or substituted with 1, 2 or 3 substituents selected from halogen, —CF₃, —OCF₃ and —OCH₃;
R³ is selected from the group consisting of:
(1) hydrogen,
(2) fluoro,
(3) chloro,
(4) bromo,
(5) —CF₃,
(6) —OCF₃,
(7) —CN,
(8) —OR⁷,
(9) —SO₂R⁷, and
(10) —SR⁷;
R⁵ is C₂-C₄ alkyl, wherein each alkyl carbon is unsubstituted or substituted with 1, 2 or 3 fluoro substituents; and
R⁷ is selected from a group consisting of:
(1) —C₁₋₆alkyl, and
(2) —C₃₋₆cycloalkyl.

In yet another embodiment of the present invention, the invention relates to the compound of structural formula IC:

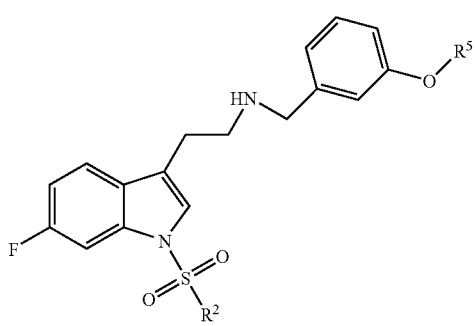

IC or a pharmaceutically acceptable salt thereof, wherein:
R² is selected from:
(1) methyl,
(2) ethyl,
(3) isopropyl, and
(4) phenyl,
wherein phenyl is unsubstituted or substituted with 1, 2 or 3 substituents selected from halogen, —CF₃, —OCF₃ and —OCH₃; and
R⁵ is selected from the group consisting of:
(1) —C₁-C₆alkyl,
(2) —C₁-C₆alkenyl,
(3) phenyl, and
(4) benzyl,
wherein each alkyl, alkenyl, phenyl and benzyl is unsubstituted or substituted on each carbon with 1, 2 or 3 substituents selected from: halogen.

In a subclass of this class, R⁵ is C₂₋₄ alkyl, wherein each alkyl carbon is unsubstituted or substituted with 1, 2 or 3 fluoro substituents.

"Alkyl", as well as other groups having the prefix "alk", such as alkoxy, alkanoyl, means carbon chains of up to 10 carbons which may be linear or branched or combinations thereof. Examples of alkyl groups include methyl, ethyl, n-propyl, isopropyl, butyl, isobutyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Cycloalkyl" means mono- or bicyclic or bridged saturated carbocyclic rings, each having from 3 to 10 carbon atoms. Examples of cycloalkyl include cyclopropyl, cyclobutyl, cyclopentyl, cyclohexyl, cycloheptyl, cyclooxtyl, tetrahydronaphthyl, decahydronaphthyl, bicycloand the like. In one embodiment of the present invention, cycloalkyl is selected from cyclopropyl, cyclobutyl, cyclopentyl, cyclohexyl, and 1,2,3,4-tetrahydronaphthyl.

"Aryl" means mono- or bicyclic aromatic rings containing only carbon atoms. Examples of aryl include phenyl, naphthyl, and the like.

"Heteroaryl" means an aromatic or partially aromatic heterocycle that contains at least one ring heteroatom selected from O, S, and N. Heteroaryls thus include heteroaryls fused to other kinds of rings, such as aryls, cycloalkyls, and cycloheteroalkyls that are not aromatic. Examples of heteroaryl groups include: pyrrolyl, isoxazolyl, isothiazaolyl, pyrazolyl, pyridyl, oxazolyl, oxadiazolyl, thiadiazolyl, thiazolyl, imidazolyl, triazolyl, tetrazolyl, furyl, triazinyl, thienyl, pyrimidyl, pyridazinyl, pyrazinyl, benzoxazolyl, benzothiazolyl, benzimidazolyl, benzofuranyl, dibenzylfuranyl, isobenzylfuranyl, benzopyrazolyl, benzothienyl, benzothiazolyl, furo(2,3-b)pyridyl, quinolyl, indolyl, isoquinolyl, oxazolidinyl, imidazothiathiazolyl, pyrazolylpyridyl, benzotriazolyl, methylenedioxyphenyl, hexahydrothieno-pyridinyl, thienopyridinyl, and the like. In one embodiment of the present invention, heteroaryl is selected from pyridyl, furyl, thienyl, pyrazolyl, oxazolyl, isoxazolyl, oxadiazolyl, indazolyl, oxadiazolyl, tetrazolyl, imidazolyl, indolyl, benzimidazolyl, triazolyl, and benzopyrazolyl.

"Cycloheteroalkyl" refers to a saturated or unsaturated non-aromatic ring or ring system containing at least one heteroatom selected from O, S and N, further including the oxidized forms of sulfur, namely SO and SO₂, in which the point of attachment may be carbon or nitrogen. Examples of cycloheteroalkyl include tetrahydrofuranyl, azetidinyl, perhydroazepinyl, dihydrofuranyl, dioxanyl, oxanyl, morpholinyl, 1,4-dithianyl, piperazinyl, piperidinyl, 1,3-dioxolanyl, imidazolidinyl, imidazolinyl, pyrrolinyl, pyrrolidinyl, pyranyl, tetrahydropyranyl, dihydropyranyl, oxathiolanyl, dithiolanyl, 1,3-dithianyl, oxathianyl, thiomorpholinyl, dioxidoisothiazolidinyl, azacycloheptyl, diazobicyclo[3.2.1]-octane, and hexahydroindazolyl. The cycloheteroalkyl ring may be substituted on the ring carbons and/or the ring nitrogens. In one embodiment of the present invention, cycloheteroalkyl is selected from tetrahydrofuranyl, imidazolidinyl, piperidinyl, pyrrolidinyl, isothiazolidinyl morpholinyl and thiomorpholinyl.

"Halogen" includes fluorine, chlorine, bromine and iodine. Fluoro means fluorine; chloro means chlorine, bromo means bromine and iodo means iodine.

When any variable (e.g., R¹, Rᵈ, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to:

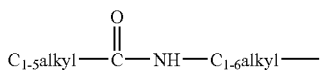

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, trifluoroacetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations.

It will be understood that, as used herein, references to the compounds of Formula I are meant to also include the pharmaceutically acceptable salts.

Compounds of the present invention are modulators of the 5-HT$_6$ receptor. In particular, the compounds of structural formula I are antagonists of the 5-HT$_6$ receptor.

An "antagonist" is a compound, devoid of intrinsic regulatory activity, which produces effects by interfering with the binding of the endogenous agonist or inhibiting the action of an agonist.

Compounds of this invention are antagonists of the 5-HT$_6$ receptor and as such are therefore useful for the treatment of obesity, diabetes, metabolic disorder, bulimia, cognitive deficits, cognitive disorders, age related cognitive disorder, depression, mania, bipolar disorders, schizophrenia, anxiety, generalized anxiety disorder, panic disorder, and obsessive compulsive disorder, epilepsy, sleep disorders, attention deficit/hyperactivity disorder, and Alzheimer's disease.

The present invention provides a method for the treatment of disorders selected from the group consisting of obesity, diabetes, metabolic disorder, bulimia, cognitive deficits, cognitive disorders, age related cognitive disorder, depression, mania, bipolar disorders, schizophrenia, anxiety, generalized anxiety disorder, panic disorder, and obsessive compulsive disorder, epilepsy, sleep disorders, attention deficit/hyperactivity disorder, and Alzheimer's disease comprising the administration of a therapeutically effective amount of a 5-HT$_6$ receptor antagonist of formula I, or a pharmaceutically acceptable salt thereof, to a patient in need thereof. The present invention also provides a method for enhancing memory and cognition comprising the administration of a therapeutically effective amount of a 5-HT$_6$ receptor antagonist of formula I, or a pharmaceutically acceptable salt thereof, to a patient in need thereof. The present invention further provides a method of reducing food intake comprising administration of a therapeutically effective amount of a 5-HT$_6$ receptor antagonist of formula I, or a pharmaceutically acceptable salt thereof, to a patient in need thereof.

The present invention further provides a method for the prevention of disorders selected from the group consisting of obesity, diabetes, metabolic disorder, bulimia, cognitive deficits, cognitive disorders, age related cognitive disorder, depression, mania, bipolar disorders, schizophrenia, anxiety, generalized anxiety disorder, panic disorder, and obsessive compulsive disorder, epilepsy, sleep disorders, attention deficit/hyperactivity disorder, and Alzheimer's disease comprising the administration of a prophylactically effective amount of a 5-HT$_6$ receptor antagonist of formula I, or a pharmaceutically acceptable salt thereof, to a patient in need thereof. The present invention also provides a method for preventing memory loss comprising the administration of a therapeutically effective amount of a 5-HT$_6$ receptor antagonist of formula I, or a pharmaceutically acceptable salt thereof, to a patient in need thereof.

The terms "administration of" and or "administering a" compound should be understood to mean providing a compound of the invention or a prodrug of a compound of the invention to the individual in need of treatment.

The administration of the compound of structural formula I in order to practice the present methods of therapy is carried out by administering an effective amount of the compound of structural formula I to the mammalian patient in need of such treatment or prophylaxis. The need for a prophylactic administration according to the methods of the present invention is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 100 mg in one embodiment from about 0.01 mg to about 50 mg, and in another embodiment from 0.1 mg to 10 mg of a compound of Formula I per kg of body weight per day.

In the case where an oral composition is employed, a suitable dosage range is, e.g. from about 0.01 mg to about 1000 mg of a compound of Formula I per day. In one embodiment, the range is from about 0.1 mg to about 10 mg per day. For oral administration, the compositions are preferably provided in the form of tablets containing from 0.01 to 1,000 mg, preferably 0.01, 0.05, 0.1, 0.5, 1, 2, 2.5, 3, 4, 5, 6, 7, 8, 9, 10, 12, 12.5, 15, 20, 25, 30, 40, 50, 100, 250, 500, 750 or 1000 milligrams of the active ingredient for the symptomatic adjustment of the dosage to the patient to be treated.

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, particularly a human or companion animal such as a dog or cat, with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. By "pharmaceutically acceptable" it is meant the carrier, diluent or excipient must be compatible with the other ingredients of the formulation and not deleterious to the recipient thereof. The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers, or as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, solutions, ointments, gels, lotions, dusting powders, and the like. The topical pharmaceutical compositions containing the compounds of the present invention ordinarily include about 0.005% to 5% by weight of the active compound in admixture with a pharmaceutically acceptable vehicle. Transdermal skin patches useful for administering the compounds of the present invention include those well known to those of ordinary skill in that art.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules (including timed release and sustained release formulations), pills, cachets, powders, granules or tablets each containing a predetermined amount of the active ingredient, as a powder or granules or as a solution or a suspension in an aqueous liquid, a non-aqueous liquid, an oil-in-water emulsion or a water-in-oil liquid emulsion, including elixirs, tinctures, solutions, suspensions, syrups and emulsions. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet cachet or capsule contains from about 0.01 to 1,000 mg, particularly 0.01, 0.05, 0.1, 0.5, 1.0, 2, 2.5, 3, 4, 5, 6, 7, 8, 9, 10, 12, 15, 25, 30, 40, 50, 75, 100, 125, 150, 175, 180, 200, 225, 250, 500, 750 and 1,000 milligrams of the active ingredient for the symptomatic adjustment of the dosage to the patient to be treated.

Additional suitable means of administration of the compounds of the present invention include injection, intravenous bolus or infusion, intraperitoneal, subcutaneous, intramuscular, intranasal, and topical, with or without occlusion.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

The dose may be administered in a single daily dose or the total daily dosage may be administered in divided doses of two, three or four times daily. Furthermore, based on the properties of the individual compound selected for administration, the dose may be administered less frequently, e.g., weekly, twice weekly, monthly, etc. The unit dosage will, of course, be correspondingly larger for the less frequent administration.

When administered via intranasal routes, transdermal routes, by rectal or vaginal suppositories, or through a continual intravenous solution, the dosage administration will, of course, be continuous rather than intermittent throughout the dosage regimen.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Capsule | mg/capsule |
|---|---|
| Compound of Formula I | 25 |
| Lactose Powder | 573.5 |
| Magnesium Stearate | 1.5 |
| | 600 |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Aerosol | Per canister |
|---|---|
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I include, but are not limited to: antipsychotic agents, cognition enhancing agents, anti-migraine agents, anti-asthmatic agents, antiinflammatory agents, anxiolytics, anti-Parkinson's agents, anti-epileptics, anorectic agents, serotonin reuptake inhibitors, other anti-obesity agents, as well as antidiabetic agents, lipid lowering agents, and antihypertensive agents which may be administered separately or in the same pharmaceutical compositions.

The present invention also provides a method for the treatment or prevention of a 5-HT$_6$ receptor modulator mediated disease, which method comprises administration to a patient in need of such treatment or at risk of developing a 5-HT$_6$ receptor modulator mediated disease of an amount of a 5-HT$_6$ receptor modulator and an amount of one or more active ingredients, such that together they give effective relief.

In a further aspect of the present invention, there is provided a pharmaceutical composition comprising a 5-HT$_6$ receptor modulator and one or more active ingredients, together with at least one pharmaceutically acceptable carrier or excipient.

Thus, according to a further aspect of the present invention there is provided the use of a 5-HT$_6$ receptor modulator and one or more active ingredients for the manufacture of a medicament for the treatment or prevention of a 5-HT$_6$ modulator mediated disease. In a further or alternative aspect of the present invention, there is therefore provided a product comprising a 5-HT$_6$ receptor modulator and one or more active ingredients as a combined preparation for simultaneous, separate or sequential use in the treatment or prevention of 5-HT$_6$ receptor modulator mediated disease. Such a combined preparation may be, for example, in the form of a twin pack.

It will be appreciated that for the treatment or prevention of eating disorders, including obesity, bulimia nervosa and compulsive eating disorders, a compound of the present invention may be used in conjunction with other anorectic agents.

The present invention also provides a method for the treatment or prevention of eating disorders, which method comprises administration to a patient in need of such treatment an amount of a compound of the present invention and an amount of an anorectic agent, such that together they give effective relief.

Suitable anorectic agents of use in combination with a compound of the present invention include, but are not limited to, a minorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof. A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof. Particular halogenated amphetamine derivatives of use in combination with a compound of the present invention include: fenfluramine and dexfenfluramine, and pharmaceutically acceptable salts thereof.

The present invention also provides a method for the treatment or prevention of obesity, which method comprises administration to a patient in need of such treatment an amount of a compound of the present invention and an amount of another agent useful in treating obesity and obesity-related disorders, such that together they give effective relief.

Suitable agents of use in combination with a compound of the present invention, include, but are not limited to:

(a) anti-diabetic agents such as (1) PPARγ agonists such as glitazones (e.g. ciglitazone; darglitazone; englitazone; isaglitazone (MCC-555); pioglitazone (ACTOS); rosiglitazone (AVANDIA); troglitazone; rivoglitazone, BRL49653; CLX-0921; 5-BTZD, GW-0207, LG-100641, R483, and LY-300512, and the like and compounds disclosed in WO97/10813, 97/27857, 97/28115, 97/28137, 97/27847, 03/000685, and 03/027112 and SPPARMS (selective PPAR gamma modulators) such as T131 (Amgen), FK614 (Fujisawa), netoglitazone, and metaglidasen; (2) biguanides such as buformin; metformin; and phenformin, and the like; (3) protein tyrosine phosphatase-1B (PTP-1B) inhibitors such as ISIS 113715, A-401674, A-364504, IDD-3, IDD 2846, KP-40046, KR61639, MC52445, MC52453, C7, OC-060062, OC-86839, OC29796, TTP-277BC1, and those agents disclosed in WO 04/041799, 04/050646, 02/26707, 02/26743, 04/092146, 03/048140, 04/089918, 03/002569, 04/065387, 04/127570, and US 2004/167183; (4) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (5) meglitinides such as repaglinide, metiglinide (GLUFAST) and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like; (7) alpha-amylase inhibitors such as tendamistat, trestatin, and A1-3688, and the like; (8) insulin secreatagogues such as linogliride nateglinide, mitiglinide (GLUFAST), ID1101 A-4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin glargine, insulin zinc suspension (lente and ultralente); Lys-Pro insulin, GLP-1 (17-36), GLP-1 (73-7) (insulintropin); GLP-1 (7-36)-NH$_2$) exenatide/Exendin-4, Exenatide LAR, Linaglutide, AVE0010, CJC 1131, BIM51077, CS 872, TH0318, BAY-694326, GP010, ALBUGON (GLP-1 fused to albumin), HGX-007 (Epac agonist), S-23521, and compounds disclosed in WO 04/022004, WO 04/37859, and the like; (12) non-thiazolidinediones such as JT-501, and farglitazar (GW-2570/GI-262579), and the like; (13) PPARα/γ dual agonists such as AVE 0847, CLX-0940, GW-1536, GW1929, GW-2433, KRP-297, L-796449, LBM 642, LR-90, LY510919, MK-0767, ONO 5129, SB 219994, TAK-559, TAK-654, 677954 (GlaxoSmithkline), E-3030 (Eisai), LY510929 (Lilly), AK109 (Asahi), DRF2655 (Dr. Reddy), DRF8351 (Dr. Reddy), MC3002 (Maxocore), TY51501 (ToaEiyo), naveglitazar, muraglitizar, peliglitazar, tesaglitazar (GALIDA), reglitazar (JTT-501), chiglitazar, and those disclosed in WO 99/16758, WO 99/19313, WO 99/20614, WO 99/38850, WO 00/23415, WO 00/23417, WO 00/23445, WO 00/50414, WO 01/00579, WO 01/79150, WO 02/062799, WO 03/033481, WO 03/033450, WO 03/033453; and (14) other insulin sensitizing drugs; (15) VPAC2 receptor agonists; (16) GLK modulators, such as PSN105, RO 281675, RO 274375 and those disclosed in WO 03/015774, WO 03/000262, WO 03/055482, WO 04/046139, WO 04/045614, WO 04/063179, WO 04/063194, WO 04/050645, and the like; (17) retinoid modulators such as those disclosed in WO 03/000249; (18) GSK 3beta/GSK 3 inhibitors such as 4-[2-(2-bromophenyl)-4-(4-fluorophenyl -1H-imidazol-5-yl]pyridine, CT21022, CT20026, CT-98023, SB-216763, SB410111, SB-675236, CP-70949, XD4241 and those compounds disclosed in WO 03/037869, 03/03877, 03/037891, 03/024447, 05/000192, 05/019218 and the like; (19) glycogen phosphorylase (HGLPa) inhibitors, such as AVE 5688, PSN 357, GPi-879, those disclosed in WO 03/037864, WO 03/091213, WO 04/092158, WO 05/013975, WO 05/013981, US 2004/0220229, and JP 2004-196702, and the like; (20) ATP consumption promotors such as those disclosed in WO 03/007990; (21) fixed combinations of PPAR γ agonists and metformin such as AVANDAMET; (22) PPAR pan agonists such as GSK 677954; (23) GPR40 (G-protein coupled receptor 40) also called SNORF 55 such as BG 700, and those disclosed in WO 04/041266, 04/022551, 03/099793; (24) GPR119 (G-protein coupled receptor 119, also called RUP3; SNORF 25) such as RUP3, HGPRBMY26, PFI 007, SNORF 25; (25) adenosine receptor 2B antagonists such as ATL-618, AT1-802, E3080, and the like; (26) carnitine palmitoyl transferase inhibitors such as ST 1327, and ST 1326, and the like; (27) Fructose 1,6-bisphosphohatase inhibitors such as CS-917, MB7803, and the like; (28) glucagon antagonists such as AT77077, BAY 694326, GW 4123X, NN2501, and those disclosed in WO 03/064404, WO 05/00781, US 2004/0209928, US 2004/029943, and the like; (30) glucose-6-phosphase inhibitors; (31) phosphoenolpyruvate carboxykinase (PEPCK) inhibitors; (32) pyruvate dehydrogenase kinase (PDK) activators; (33) RXR agonists such as MC1036, CS00018, JNJ 10166806, and those disclosed in WO 04/089916, U.S. Pat. No. 6,759,546, and the like; (34) SGLT inhibitors such as AVE 2268, KGT 1251, T1095/RWJ 394718; (35) BLX-1002; (36) alpha glucosidase inhibitors; (37) glucagon receptor agonists; and (38) glucokinase activators;

(b) lipid lowering agents such as (1) bile acid sequestrants such as, cholestyramine, colesevelem, colestipol, dialkylaminoalkyl derivatives of a cross-linked dextran; Colestid®; LoCholest®; and Questran®, and the like; (2) HMG-CoA reductase inhibitors such as atorvastatin, itavastatin, pitavastatin, fluvastatin, lovastatin, pravastatin, rivastatin, rosuvastatin, simvastatin, rosuvastatin (ZD-4522), and the like, particularly simvastatin; (3) HMG-CoA synthase inhibitors; (4) cholesterol absorption inhibitors such as FMVP4 (Forbes Medi-Tech), KT6-971 (Kotobuki Pharmaceutical), FM-VA12 (Forbes Medi-Tech), FM-VP-24 (Forbes Medi-Tech), stanol esters, beta-sitosterol, sterol glycosides such as tiqueside; and azetidinones such as ezetimibe, and those disclosed in WO 04/005247 and the like; (5) acyl coenzyme A-cholesterol acyl transferase (ACAT) inhibitors such as avasimibe, eflucimibe, pactimibe (KY505), SMP 797 (Sumitomo), SM32504 (Sumitomo), and those disclosed in WO 03/091216, and the like; (6) CETP inhibitors such as JTT 705 (Japan Tobacco), torcetrapib, CP 532,632, BAY63-2149 (Bayer), SC 591, SC 795, and the like; (7) squalene synthetase inhibitors; (8) anti-oxidants such as probucol, and the like; (9) PPARα agonists such as beclofibrate, benzafibrate, ciprofibrate, clofibrate, etofibrate, fenofibrate, gemcabene, and gemfibrozil, GW 7647, BM 170744 (Kowa), LY518674 (Lilly), GW590735 (GlaxoSmithkline), KRP-101 (Kyorin), DRF10945 (Dr. Reddy), NS-220/R1593 (Nippon Shinyaku/Roche, ST1929 (Sigma Tau) MC3001/MC3004 (MaxoCore Pharmaceuticals, gemcabene calcium, other fibric acid derivatives, such as Atromid®, Lopid® and Tricor®, and those disclosed in U.S. Pat. No. 6,548,538, and the like; (10) FXR receptor modulators such as GW 4064 (GlaxoSmithkline), SR 103912, QRX401, LN-6691 (Lion Bioscience), and those disclosed in WO 02/064125, WO 04/045511, and the like; (11) LXR receptor modulators such as GW 3965 (GlaxoSmithkline), T9013137, and XTC0179628 (X-Ceptor Therapeutics/Sanyo), and those disclosed in WO 03/031408, WO 03/063796, WO 04/072041, and the like; (12) lipoprotein synthesis inhibitors such as niacin; (13) renin angiotensin system inhibitors; (14) PPAR δ partial agonists, such as those disclosed in WO 03/024395; (15) bile acid reabsorption inhibitors, such as BARI 1453, SC435, PHA384640, S8921, AZD7706, and the like; and bile acid sequesterants such as colesevelam (WELCHOL/CHOLESTAGEL), (16) PPARδ agonists such as GW 501516 (Ligand, GSK), GW 590735, GW-0742 (GlaxoSmithkline), T659 (Amgen/Tularik), LY934 (Lilly), NNC610050 (Novo Nordisk) and those disclosed in WO97/28149, WO 01/79197, WO 02/14291, WO 02/46154, WO 02/46176, WO 02/076957, WO 03/016291, WO 03/033493, WO 03/035603, WO 03/072100, WO 03/097607, WO 04/005253, WO 04/007439, and JP10237049, and the like; (17) triglyceride synthesis inhibitors; (18) microsomal triglyceride transport (MTTP) inhibitors, such as implitapide, LAB687, JTT130 (Japan Tobacco), CP346086, and those disclosed in WO 03/072532, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists including HM74A receptor agonists; (25) PPAR modulators such as those disclosed in WO 01/25181, WO 01/79150, WO 02/79162, WO 02/081428, WO 03/016265, WO 03/033453; (26) niacin-bound chromium, as disclosed in WO 03/039535; (27) substituted acid derivatives disclosed in WO 03/040114; (28) infused HDL such as LUV/ETC -588 (Pfizer), APO-A1 Milano/ETC216 (Pfizer), ETC-642 (Pfizer), ISIS301012, D4F (Bruin Pharma), synthetic trimeric ApoA1, Bioral Apo A1 targeted to foam cells, and the like; (29) IBAT inhibitors such as BARI143/HMR145A/HMR1453 (Sanofi-Aventis, PHA384640E (Pfizer), S8921 (Shionogi) AZD7806 (AstrZeneca), AK105 (Asah Kasei), and the like; (30) Lp -PLA 2 inhibitors such as SB480848 (GlaxoSmithkline), 659032 (GlaxoSmithkline), 677116 (GlaxoSmithkline), and the like; (31) other agents which affect lipic composition including ETC1001/ESP31015 (Pfizer), ESP-55016 (Pfizer), AGI1067 (AtheroGenics), AC3056 (Amylin), AZD4619 (AstrZeneca); and (c) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, and the like;

(8) angiotensin II receptor antagonists such as candesartan, eprosartan, irbesartan, losartan, pratosartan, tasosartan, telmisartan, valsartan, and EXP-3137, FI6828K, and RNH6270, and the like; (9) α/β adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XEN010, and the like; (11) alpha 2 agonists such as lofexidine, tiamenidine, moxonidine, rilmenidine and guanobenz, and the like; (12) aldosterone inhibitors, and the like; (13) angiopoietin-2-binding agents such as those disclosed in WO 03/030833; and (d) anti-obesity agents, such as (1) 5-HT (serotonin) transporter inhibitors, such as paroxetine, fluoxetine, fenfluramine, fluvoxamine, sertraline, and imipramine, and those disclosed in WO 03/00663, as well as serotonin/noradrenaline re uptake inhibitors such as sibutramine (MERIDIA/REDUCTIL) and dopamine uptake inhibitor/Norepenephrine uptake inhibitors such as radafaxine hydrochloride, 353162 (GlaxoSmithkline), and the like; (2) NE (norepinephrine) transporter inhibitors, such as GW 320659, despiramine, talsupram, and nomifensine; (3) CB1 (cannabinoid-1 receptor) antagonist/inverse agonists, such as rimonabant (ACCOMPLIA Sanofi Synthelabo), SR-147778 (Sanofi Synthelabo), AVE1625 (Sanofi-Aventis), BAY 65-2520 (Bayer), SLV 319 (Solvay), SLV326 (Solvay), CP945598 (Pfizer), E-6776 (Esteve), O1691 (Organix), ORG14481 (Organon), VER24343 (Vernalis), NESS0327 (Univ of Sassari/Univ of Cagliari), taranabant, and those disclosed in U.S. Pat. Nos. 4,973,587, 5,013,837, 5,081,122, 5,112,820, 5,292,736, 5,532,237, 5,624,941, 6,028,084, and 6,509367; and WO 96/33159, WO97/29079, WO98/31227, WO 98/33765, WO98/37061, WO98/41519, WO98/43635, WO98/43636, WO99/02499, WO00/10967, WO00/10968, WO 01/09120, WO 01/58869, WO 01/64632, WO 01/64633, WO 01/64634, WO 01/70700, WO 01/96330, WO 02/076949, WO 03/006007, WO 03/007887, WO 03/020217, WO 03/026647, WO 03/026648, WO 03/027069, WO 03/027076, WO 03/027114, WO 03/037332, WO 03/040107, WO 04/096763, WO 04/111039, WO 04/111033, WO 04/111034, WO 04/111038, WO 04/013120, WO 05/000301, WO 05/016286, WO 05/066126 and EP-658546 and the like; (4) ghrelin agonists/antagonists, such as BVT81-97 (BioVitrum), RC1291 (Rejuvenon), SRD-04677 (Sumitomo), unacylated ghrelin (TheraTechnologies), and those disclosed in WO 01/87335, WO 02/08250, WO 05/012331, and the like; (5) H3 (histamine H3) antagonist/inverse agonists, such as thioperamide, 3-(1H-imidazol-4-yl)propyl N-(4-pentenyl)carbamate), clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in WO 03/024928 and WO 03/024929; (6) melanin-concentrating hormone 1 receptor (MCH1R) antagonists, such as T-226296 (Takeda), T71 (Takeda/Amgen), AMGN-608450, AMGN-503796 (Amgen), 856464 (GlaxoSmithkline), A224940 (Abbott), A798 (Abbott), ATC0175/AR224349 (Arena Pharmaceuticals), GW803430 (GlaxoSmithkine), NBI-1A (Neurocrine Biosciences), NGX-1 (Neurogen), SNP-7941 (Synaptic), SNAP9847 (Synaptic), T-226293 (Schering Plough), TPI-1361-17 (Saitama Medical School/University of California Irvine), and those disclosed WO 01/21169, WO 01/82925, WO 01/87834, WO 02/051809, WO 02/06245, WO 02/076929, WO 02/076947, WO 02/04433, WO 02/51809, WO 02/083134, WO 02/094799, WO 03/004027, WO 03/13574, WO 03/15769, WO 03/028641, WO 03/035624, WO 03/033476, WO 03/033480, WO 04/004611, WO 04/004726, WO 04/011438, WO 04/028459, WO 04/034702, WO 04/039764, WO 04/052848, WO 04/087680; and Japanese Patent Application Nos. JP 13226269, JP 1437059, JP2004315511, and the like; (7) MCH2R (melanin concentrating hormone 2R) agonist/antagonists; (8) NPY1 (neuropeptide Y Y1) antagonists, such as BMS205749, BIBP3226, J-115814, BIBO 3304, LY-357897, CP-671906, and GI-264879A; and those disclosed in U.S. Pat. No. 6,001,836; and WO 96/14307, WO 01/23387, WO 99/51600, WO 01/85690, WO 01/85098, WO 01/85173, and WO 01/89528; (9) NPY5 (neuropeptide Y Y5) antagonists, such as 152,804, S2367 (Shionogi), E-6999 (Esteve), GW-569180A, GW-594884A (GlaxoSmithkline), GW-587081×, GW-548118×; FR 235,208; FR226928, FR 240662, FR252384; 1229U91, GI-264879A, CGP71683A, C-75 (Fasgen) LY-377897, LY366377, PD-160170, SR-120562A, SR-120819A, S2367 (Shionogi), JCF-104, and H409/22; and those compounds disclosed in U.S. Pat. Nos. 6,140,354, 6,191,160, 6,258,837, 6,313,298, 6,326,375, 6,329,395, 6,335,345, 6,337,332, 6,329,395, and 6,340,683; and EP-01010691, EP-01044970, and FR252384; and PCT Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, WO 02/051806, WO 02/094789, WO 03/009845, WO 03/014083, WO 03/022849, WO 03/028726, WO 05/014592, WO 05/01493; and Norman et al., J. Med. Chem. 43:4288-4312 (2000); (10) leptin, such as recombinant human leptin (PEG-OB, Hoffman La Roche) and recombinant methionyl human leptin (Amgen); (11) leptin derivatives, such as those disclosed in U.S. Pat. Nos. 5,552,524; 5,552,523; 5,552,522; 5,521,283; and WO 96/23513; WO 96/23514; WO 96/23515; WO 96/23516; WO 96/23517; WO 96/23518; WO 96/23519; and WO 96/23520; (12) opioid antagonists, such as nalmefene (Revex®), 3-methoxynaltrexone, naloxone, and naltrexone; and those disclosed in WO 00/21509; (13) orexin antagonists, such as SB-334867-A (GlaxoSmithkline); and those disclosed in WO 01/96302, 01/68609, 02/44172, 02/51232, 02/51838, 02/089800, 02/090355, 03/023561, 03/032991, 03/037847, 04/004733, 04/026866, 04/041791, 04/085403, and the like; (14) BRS3 (bombesin receptor subtype 3) agonists; (15) CCK-A (cholecystokinin-A) agonists, such as AR -R15849, GI 181771, JMV-180, A-71378, A-71623, PD170292, PD 149164, SR146131, SR125180, butabindide, and those disclosed in U.S. Pat. No. 5,739,106; (16) CNTF (ciliary neurotrophic factors), such as GI-181771 (Glaxo-SmithKline); SR146131 (Sanofi Synthelabo); butabindide; and PD170,292, PD 149164 (Pfizer); (17) CNTF derivatives, such as axokine (Regeneron); and those disclosed in WO 94/09134, WO 98/22128, and WO 99/43813; (18) GHS (growth hormone secretagogue receptor) agonists, such as NN703, hexarelin, MK-0677, SM-130686, CP-424,391, L-692,429 and L-163,255, and those disclosed in U.S. Pat. No. 6,358,951, U.S. Patent Application Nos. 2002/049196 and 2002/022637; and WO 01/56592, and WO 02/32888;

(19) 5-HT2c (serotonin receptor 2c) agonists, such as APD3546/AR10A (Arena Pharmaceuticals), ATH88651 (Athersys), ATH88740 (Athersys), BVT933 (Biovitrum/GSK), DPCA37215 (BMS), IK264; LY448100 (Lilly), PNU 22394; WAY 470 (Wyeth), WAY629 (Wyeth), WAY161503 (Biovitrum), R-1065, VR1065 (Vernalis/Roche) YM 348; and those disclosed in U.S. Pat. No. 3,914,250; and PCT Publications 01/66548, 02/36596, 02/48124, 02/10169, 02/44152; 02/51844, 02/40456, 02/40457, 03/057698, 05/000849, and the like; (20) Mc3r (melanocortin 3 receptor) agonists; (21) Mc4r (melanocortin 4 receptor) agonists, such as CHIR86036 (Chiron), CHIR915 (Chiron); ME-10142 (Melacure), ME-10145 (Melacure), HS-131 (Melacure), NBI72432 (Neurocrine Biosciences), NNC 70-619 (Novo Nordisk), TTP2435 (Transtech)and those disclosed in PCT Publications WO 99/64002, 00/74679, 01/991752, 01/0125192, 01/52880, 01/74844, 01/70708, 01/70337, 01/91752, 01/010842, 02/059095, 02/059107, 02/059108, 02/059117, 02/062766, 02/069095, 02/12166, 02/11715, 02/12178, 02/15909, 02/38544, 02/068387, 02/068388, 02/067869, 02/081430, 03/06604, 03/007949, 03/009847, 03/009850, 03/013509, 03/031410, 03/094918, 04/028453, 04/048345, 04/050610, 04/075823, 04/083208, 04/089951, 05/000339, and EP 1460069, and US 2005049269, and JP2005042839, and the like; (22) monoamine reuptake inhibitors, such as sibutratmine (Meridia®/Reductil®) and salts thereof, and those compounds disclosed in U.S. Pat. Nos. 4,746,680, 4,806,570, and 5,436,272, and U.S. Patent Publication No. 2002/0006964, and WO 01/27068, and WO 01/62341; (23) serotonin reuptake inhibitors, such as dexfenfluramine, fluoxetine, and those in U.S. Pat. No. 6,365,633, and WO 01/27060, and WO 01/162341; (24) GLP-1 (glucagon-like peptide 1) agonists; (25) Topiramate (Topimax®); (26) phytopharm compound 57 (CP 644,673); (27) ACC2 (acetyl-CoA carboxylase-2) inhibitors; (28) β3 (beta adrenergic receptor 3) agonists, such as rafebergron/AD9677/TAK677 (Dainippon/Takeda), CL-316,243, SB 418790, BRL-37344, L-796568, BMS-196085, BRL-35135A, CGP12177A, BTA-243, GRC1087 (Glenmark Pharmaceuticals) GW 427353 (solabegron hydrochloride), Trecadrine, Zeneca D7114, N-5984 (Nisshin Kyorin), LY-377604 (Lilly), KT07924 (Kissei), SR 59119A, and those disclosed in U.S. Pat. Nos. 5,705,515, 5,451,677; and WO94/18161, WO95/29159, WO97/46556, WO98/04526 WO98/32753, WO 01/74782, WO 02/32897, WO 03/014113, WO 03/016276, WO 03/016307, WO 03/024948, WO 03/024953, WO 03/037881, WO 04/108674, and the like; (29) DGAT1 (diacylglycerol acyltransferase 1) inhibitors; (30) DGAT2 (diacylglycerol acyltransferase 2) inhibitors; (31) FAS (fatty acid synthase) inhibitors, such as Cerulenin and C75; (32) PDE (phosphodiesterase) inhibitors, such as theophylline, pentoxifylline, zaprinast, sildenafil, aminone, milrinone, cilostamide, rolipram, and cilomilast, as well as those described in WO 03/037432, WO 03/037899; (33) thyroid hormone β agonists, such as KB-2611 (KaroBioBMS), and those disclosed in WO 02/15845; and Japanese Patent Application No. JP 2000256190; (34) UCP-1 (uncoupling protein 1), 2, or 3 activators, such as phytanic acid, 4-[(E) -2-(5,6,7,8-tetrahydro-5,5,8,8-tetramethyl-2-napthalenyl)-1-propenyl]benzoic acid (TTNPB), and retinoic acid; and those disclosed in WO 99/00123; (35) acyl-estrogens, such as oleoyl-estrone, disclosed in del Mar-Grasa, M. et al., Obesity Research, 9:202-9 (2001); (36) glucocorticoid receptor antagonists, such as CP472555 (Pfizer), KB 3305, and those disclosed in WO 04/000869, WO 04/075864, and the like; (37) 11β HSD-1 (11-beta hydroxy steroid dehydrogenase type 1) inhibitors, such as BVT 3498 (AMG 331), BVT 2733, 3-(1-adamantyl)- 4-ethyl-5-(ethylthio)-4H-1,2,4-triazole, 3-(1-adamantyl)-5-(3,4,5-trimethoxyphenyl)-4-methyl-4H-1,2,4-triazole, 3-adamantanyl-4,5,6,7,8,9,10,11,12,3a-decahydro-1,2,4-triazolo[4,3-a][11]annulene, and those compounds disclosed in WO 01/90091, 01/90090, 01/90092, 02/072084, 04/011410, 04/033427, 04/041264, 04/027047, 04/056744, 04/065351, 04/089415, 04/037251, and the like; (38) SCD-1 (stearoyl-CoA desaturase-1) inhibitors; (39) dipeptidyl peptidase IV (DPP-4) inhibitors, such as isoleucine thiazolidide, valine pyrrolidide, sitagliptin, saxagliptin, NVP-DPP728, LAF237 (vildagliptin), P93/01, TSL 225, TMC-2A/2B/2C, FE 999011, P9310/K364, VIP 0177, SDZ 274-444, GSK 823093, E 3024, SYR 322, TS021, SSR 162369, GRC 8200, K579, NN7201, CR 14023, PHX 1004, PHX 1149, PT-630, SK-0403; and the compounds disclosed in WO 02/083128, WO 02/062764, WO 02/14271, WO 03/000180, WO 03/000181, WO 03/000250, WO 03/002530, WO 03/002531, WO 03/002553, WO 03/002593, WO 03/004498, WO 03/004496, WO 03/005766, WO 03/017936, WO 03/024942, WO 03/024965, WO 03/033524, WO 03/055881, WO 03/057144, WO 03/037327, WO 04/041795, WO 04/071454, WO 04/0214870, WO 04/041273, WO 04/041820, WO 04/050658, WO 04/046106, WO 04/067509, WO 04/048532, WO 04/099185, WO 04/108730, WO 05/009956, WO 04/09806, WO 05/023762, US 2005/043292, and EP 1 258 476; (40) lipase inhibitors, such as tetrahydrolipstatin (orlistat/XENICAL), ATL962 (Alizyme/Takeda), GT389255 (Genzyme/Peptimmune) Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC 80267, and those disclosed in WO 01/77094, WO 04/111004, and U.S. Pat. Nos. 4,598,089, 4,452,813, 5,512,565, 5,391,571, 5,602,151, 4,405,644, 4,189,438, and 4,242,453, and the like; (41) fatty acid transporter inhibitors; (42) dicarboxylate transporter inhibitors; (43) glucose transporter inhibitors; and (44) phosphate transporter inhibitors; (45) anorectic bicyclic compounds such as 1426 (Aventis) and 1954 (Aventis), and the compounds disclosed in WO 00/18749, WO 01/32638, WO 01/62746, WO 01/62747, and WO 03/015769; (46) peptide YY and PYY agonists such as PYY336 (Nastech/Merck), AC162352 (IC Innovations/Curis/Amylin), TM30335/TM30338 (7TM Pharma), PYY336 (Emisphere Tehcnologies), pegylated peptide YY3-36, those disclosed in WO 03/026591, 04/089279, and the like; (47) lipid metabolism modulators such as maslinic acid, erythrodiol, ursolic acid uvaol, betulinic acid, betulin, and the like and compounds disclosed in WO 03/011267; (48) transcription factor modulators such as those disclosed in WO 03/026576; (49) Mc5r (melanocortin 5 receptor) modulators, such as those disclosed in WO 97/19952, WO 00/15826, WO 00/15790, US 20030092041, and the like; (50) Brain derived neutotropic factor (BDNF), (51) Mc1r (melanocortin 1 receptor modulators such as LK-184 (Proctor & Gamble), and the like; (52) other 5-HT$_6$ antagonists such as BVT74316 (BioVitrum), BVT5182c (BioVitrum), E-6795 (Esteve), E-6814 (Esteve), SB399885 (GlaxoSmithkline), SB271046 (GlaxoSmithkline), RO-046790 (Roche), and the like; (53) fatty acid transport protein 4 (FATP4); (54) acetyl-CoA carboxylase (ACC) inhibitors such as CP640186, CP610431, CP640188 (Pfizer); (55) C-terminal growth hormone fragments such as AOD9604 (Monash Univ/Metabolic Pharmaceuticals), and the like; (56) oxyntomodulin; (57) neuropeptide FF receptor antagonists such as those disclosed in WO 04/083218, and the like; (58) amylin agonists such as Symlin/pramlintide/AC137 (Amylin); (59) Hoodia and trichocaulon extracts; (60) BVT74713 and other gut lipid appetite suppressants; (61)

dopamine agonists such as bupropion (WELLBUTRIN/ GlaxoSmithkline); (62) zonisamide (ZONEGRAN/Dainippon/Elan), and the like.

Specific compounds of use in combination with a compound of the present invention include: simvastatin, mevastatin, ezetimibe, atorvastatin, sitagliptin, metformin, sibutramine, orlistat, Qnexa, topiramate, naltrexone, bupriopion, phentermine, and losartan, losartan with hydrochlorothiazide. Specific CB1 antagonists/inverse agonists of use in combination with a compound of the present invention include: those described in WO03/077847, including: N-[3-(4-chlorophenyl)-2(S)-phenyl-1(S)-methylpropyl]-2-(4-trifluoromethyl-2-pyrimidyloxy)-2-methylpropanamide, N-[3-(4-chlorophenyl)-2-(3-cyanophenyl)-1-methylpropyl]-2-(5-trifluoromethyl-2-pyridyloxy)-2-methylpropanamide, N-[3-(4-chlorophenyl)-2-(5-chloro-3-pyridyl)-1-methylpropyl]-2-(5-trifluoromethyl-2-pyridyloxy)-2-methylpropanamide, and pharmaceutically acceptable salts thereof; as well as those in WO05/000809, which includes the following: 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]azetidin-3-yl}-1-(3,5-difluorophenyl)-2-methylpropan-2-ol. 3-((S)-(4-chlorophenyl) {3-[(1S)-1-(3,5-difluorophenyl)-2-hydroxy-2-methylpropyl]azetidin-1-yl}methyl)benzonitrile, 3-((S)-(4-chlorophenyl){3-[(1S)-1-(3,5-difluorophenyl)-2-fluoro-2-methylpropyl]azetidin-1-yl}methyl)benzonitrile, 3-((4-chlorophenyl){3-[1-(3,5-difluorophenyl)-2,2-dimethylpropyl]azetidin-1-yl}methyl)benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl)(3-{(1S)-2-fluoro-1-[3-fluoro-5-(4H-1,2,4-triazol-4-yl) phenyl]-2-methylpropyl}azetidin-1-yl)methyl]benzonitrile, and 5-((4-chlorophenyl) {3-[(1S)-1-(3,5-difluorophenyl)-2-fluoro-2-methylpropyl]azetidin-1-yl}methyl)thiophene-3-carbonitrile, and pharmaceutically acceptable salts thereof; as well as: 3-[(S)-(4-chlorophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,3,4-oxadiazol-2-yl)phenyl]-2-methylpropyl}azetidin-1-yl) methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-chlorophenyl)methyl] benzonitrile, 3-[(S)-(4-cyanophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol -2-yl)-5-fluorophenyl]-2-fluoro-2-methylpropyl}azetidin-1-yl)(4-cyanophenyl)methyl]benzonitrile, 3-[(S)-(4-cyanophenyl) (3-{(1S)-2-fluoro-1-[3-fluoro-5-(1,3,4-oxadiazol-2-yl) phenyl]-2-methylpropyl}azetidin-1-yl)methyl]benzonitrile, 3-[(S)-(4-chlorophenyl)(3-{(1S)-2-fluoro-1-[3-fluoro-5-(1, 2,4-oxadiazol-3-yl)phenyl]-2-methylpropyl}azetidin-1-yl) methyl]benzonitrile, 3-[(1S)-1-(1-{(S)-(4-cyanophenyl)[3-(1,2,4-oxadiazol-3-yl)phenyl]-methyl}azetidin-3-yl)-2-fluoro-2-methylpropyl]-5-fluorobenzonitrile, 5-(3-{1-[1-(diphenylmethyl)azetidin-3-yl]-2-fluoro-2-methylpropyl}-5-fluorophenyl)-1H-tetrazole, 5-(3-{1-[1-(diphenylmethyl) azetidin-3-yl]-2-fluoro-2-methylpropyl}-5-fluorophenyl)-1-methyl -1H-tetrazole, 5-(3-{1-[1-(diphenylmethyl)azetidin-3-yl]-2-fluoro-2-methylpropyl}-5-fluorophenyl)-2-methyl-2H-tetrazole, 3-[(4-chlorophenyl)(3-{2-fluoro-1-[3-fluoro-5-(2-methyl -2H-tetrazol-5-yl)phenyl]-2-methylpropyl}azetidin-1-yl)methyl]benzonitrile, 3-[(4-chlorophenyl)(3-{2-fluoro-1-[3-fluoro-5-(1-methyl-1H-tetrazol-5-yl)phenyl]-2-methylpropyl}azetidin-1-yl)methyl] benzonitrile, 3-[(4-cyanophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(2-methyl-2H-tetrazol-5-yl)phenyl]-2-methylpropyl}azetidin-1-yl)methyl] benzonitrile, 5-{3-[(S)-{3-[(1S)-1-(3-bromo-5-fluorophenyl) -2-fluoro-2-methylpropyl]azetidin-1-yl}(4-chlorophenyl)methyl]phenyl}-1,3,4-oxadiazol-2(3H)-one, 3-[(1S)-1-(1-{(S)-(4-chlorophenyl)[3-(5-oxo-4,5-dihydro-1, 3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(5-oxo-4,5-dihydro-1,3,4-oxadiazol-2-yl) phenyl]methyl}azetidin-3-yl) -2-fluoro-2-methylpropyl]-5-fluorobenzonitrile, 3-[(1S)-1-(1-{(S)-(4-cyanophenyl)[3-(1, 3,4-oxadiazol-2-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,3,4-oxadiazol-2-yl)phenyl] methyl}azetidin-3-yl)-2-fluoro -2-methylpropyl]-5-fluorobenzonitrile, 3-((1S)-1-{1-[(S)-[3-(5-amino-1,3,4-oxadiazol-2-yl)phenyl](4-chlorophenyl)methyl]azetidin-3-yl}-2-fluoro-2-methylpropyl)-5-fluorobenzonitrile, 3-((1S)-1-{1-[(S)-[3-(5-amino-1,3,4-oxadiazol-2-yl)phenyl](4-cyanophenyl)methyl]azetidin-3-yl}-2-fluoro-2-methylpropyl)-5-fluorobenzonitrile, 3-[(1S)-1-(1-{(S)-(4-cyanophenyl)[3-(1,2,4-oxadiazol-3-yl)phenyl] methyl}azetidin-3-yl)-2-fluoro-2-methylpropyl]-5-fluorobenzonitrile, 3-[(1S)-1-(1-{(S)-(4-chlorophenyl)[3-(1, 2,4-oxadiazol-3-yl)phenyl]methyl}azetidin-3-yl)-2-fluoro -2-methylpropyl]-5-fluorobenzonitrile, 5-[3-((S)-(4-chlorophenyl){3-[(1S)-1-(3,5-difluorophenyl) -2-fluoro-2-methylpropyl]azetidin-1-yl}methyl)phenyl]-1,3,4-oxadiazol-2 (3H)-one, 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one, 4-{(S)-{3-[(1S)-1-(3,5-difluorophenyl)-2-fluoro -2-methylpropyl] azetidin-1-yl}[3-(5-oxo-4,5-dihydro-1,3,4-oxadiazol-2-yl) phenyl]methyl}-benzonitrile, and pharmaceutically acceptable salts thereof.

Specific NPY5 antagonists of use in combination with a compound of the present invention include: 3-oxo-N-(5-phenyl-2-pyrazinyl)-spiro[isobenzofuran-1(3H), 4'-piperidine]-1'-carboxamide, 3-oxo-N-(7-trifluoromethylpyrido[3,2-b]pyridin-2-yl)spiro-[isobenzofuran -1(3H), 4'-piperidine]-1'-carboxamide, N-[5-(3-fluorophenyl)-2-pyrimidinyl]-3-oxospiro -[isobenzofuran-1(3H), 4'-piperidine]-1'-carboxamide, trans-3'-oxo-N-(5-phenyl-2-pyrimidinyl)spiro [cyclohexane-1,1'(3'H)-isobenzofuran]-4-carboxamide, trans-3'-oxo-N-[1-(3-quinolyl)-4-imidazolyl]spiro[cyclohexane-1,1'(3'H)-isobenzofuran]-4-carboxamide, trans-3-oxo -N-(5-phenyl-2-pyrazinyl)spiro[4-azaiso-benzofuran-1 (3H), 1'-cyclohexane]-4'-carboxamide, trans-N-[5-(3-fluorophenyl)-2-pyrimidinyl]-3-oxospiro[5-azaisobenzofuran-1(3H), 1'-cyclohexane]-4'-carboxamide, trans-N-[5-(2-fluorophenyl)-2-pyrimidinyl]-3-oxospiro[5-azaisobenzofuran-1(3H), 1'-cyclohexane]-4'-carboxamide, trans-N-[1-(3,5-difluorophenyl)-4-imidazolyl]-3-oxospiro [7-azaisobenzofuran-1(3H), 1'-cyclohexane]-4'-carboxamide, trans-3-oxo -N-(1-phenyl-4-pyrazolyl)spiro[4-azaisobenzofuran-1(3H), 1'-cyclohexane]-4'-carboxamide, trans-N-[1-(2-fluorophenyl)-3-pyrazolyl]-3-oxospiro[6-azaisobenzofuran-1(3H),1'-cyclohexane]-4'-carboxamide, trans-3-oxo-N-(1-phenyl-3-pyrazolyl)spiro[6-azaisobenzofuran-1(3H), 1'-cyclohexane]-4'-carboxamide, trans-3-oxo-N-(2-phenyl-1,2,3-triazol-4-yl)spiro[6-azaisobenzofuran-1 (3H), 1'-cyclohexane]-4'-carboxamide, and pharmaceutically acceptable salts and esters thereof.

Specific ACC-1/2 inhibitors of use in combination with a compound of the present invention include: 1'-[(4,8-dimethoxyquinolin-2-yl)carbonyl]-6-(1H-tetrazol-5-yl)spiro[chroman-2,4'-piperidin]-4-one; (5-{1'-[(4,8-dimethoxyquinolin-2-yl)carbonyl]-4-oxospiro[chroman-2,4'-piperidin]-6-yl}-2H-tetrazol-2-yl)methyl pivalate; 5-{1'-[(8-cyclopropyl-4-methoxyquinolin-2-yl)carbonyl]-4-oxospiro[chroman-2,4'-piperidin]-6-yl}nicotinic acid; 1'-(8-methoxy-4-morpholin-4-yl-2-naphthoyl)-6-(1H-tetrazol-5-yl)spiro[chroman-2,4'-piperidin]-4-one; and 1'-[(4-ethoxy-8-ethylquinolin-2-yl)carbonyl]-6-(1H-tetrazol-5-yl)spiro[chroman-2,4'-piperidin]-4-one; and pharmaceutically acceptable salts and esters thereof.

Specific MCH1R antagonist compounds of use in combination with a compound of the present invention include: 1-{4-[(1-ethylazetidin-3-yl)oxy]phenyl}-4-[(4-fluorobenzyl)oxy]pyridin-2(1H)-one, 4-[(4-fluorobenzyl)oxy]-1-{4-[(1-isopropylazetidin-3-yl)oxy]phenyl}pyridin-2(1H)-one, 1-[4-(azetidin-3-yloxy)phenyl]-4-[(5-chloropyridin-2-yl)methoxy]pyridin-2(1H)-one, 4-[(5-chloropyridin-2-yl)methoxy]-1-{4-[(1-ethylazetidin-3-yl)oxy]phenyl}pyridin-2(1H)-one, 4-[(5-chloropyridin-2-yl)methoxy]-1-{4-[(1-propylazetidin-3-yl)oxy]phenyl}pyridin-2(1H)-one, and 4-[(5-chloropyridin-2-yl)methoxy]-1-(4-{[(2S)-1-ethylazetidin-2-yl]methoxy}phenyl)pyridin-2(1H)-one, or a pharmaceutically acceptable salt thereof.

Specific DP-IV inhibitors of use in combination with a compound of the present invention are selected from 7-[(3R)-3-amino-4-(2,4,5-trifluorophenyl)butanoyl]-3-(trifluoromethyl)-5,6,7,8-tetrahydro-1,2,4-triazolo[4,3-a]pyrazine. In particular, the compound of formula I is favorably combined with 7-[(3R)-3-amino-4-(2,4,5-trifluorophenyl)butanoyl]-3-(trifluoromethyl)-5,6,7,8-tetrahydro-1,2,4-triazolo[4,3-a]pyrazine, and pharmaceutically acceptable salts thereof.

Specific H3 (histamine H3) antagonists/inverse agonists of use in combination with a compound of the present invention include: those described in WO05/077905, including: 3-{4-[(1-cyclobutyl-4-piperidinyl)oxy]phenyl}-2-ethylpyrido[2,3-d]-pyrimidin-4(3H)-one, 3-{4-[(1-cyclobutyl-4-piperidinyl)oxy]phenyl}-2-methylpyrido[4,3-d]pyrimidin-4(3H)-one, 2-ethyl-3-(4-{3-[(3S)-3-methylpiperidin-1-yl]propoxy}phenyl)pyrido[2,3-d]pyrimidin-4(3H)-one 2-methyl-3-(4-{3-[(3S)-3-methylpiperidin-1-yl]propoxy}phenyl)pyrido[4,3-d]pyrimidin-4(3H)-one, 3-{4-[(1-cyclobutyl-4-piperidinyl)oxy]phenyl}-2,5-dimethyl-4(3H)-quinazolinone, 3-{4-[(1-cyclobutyl-4-piperidinyl)oxy]phenyl}-2-methyl-5-trifluoromethyl-4(3H)-quinazolinone, 3-{4-[(1-cyclobutyl-4-piperidinyl)oxy]phenyl}-5-methoxy-2-methyl-4(3H)-quinazolinone, 3-{4-[(1-cyclobutylpiperidin-4-yl)oxy]phenyl}-5-fluoro-2-methyl-4(3H)-quinazolinone, 3-{4-[(1-cyclobutylpiperidin-4-yl)oxy]phenyl}-7-fluoro-2-methyl-4(3H)-quinazolinone, 3-{4-[(1-cyclobutylpiperidin-4-yl)oxy]phenyl}-6-methoxy-2-methyl-4(3H)-quinazolinone, 3-{4-[(1-cyclobutylpiperidin-4-yl)oxy]phenyl}-6-fluoro-2-methyl-4(3H)-quinazolinone, 3-{4-[(1-cyclobutylpiperidin-4-yl)oxy]phenyl}-8-fluoro-2-methyl-4(3H)-quinazolinone, 3-{4-[(1-cyclopentyl-4-piperidinyl)oxy]phenyl}-2-methylpyrido[4,3-d]pyrimidin-4(3H)-one, 3-{4-[(1-cyclobutylpiperidin-4-yl)oxy]phenyl}-6-fluoro-2-methylpyrido[3,4-d]pyrimidin-4(3H)-one, 3-{4-[(1-cyclobutyl-4-piperidinyl)oxy]phenyl}-2-ethylpyrido[4,3-d]pyrimidin-4(3H)-one, 6-methoxy-2-methyl-3-{4-[3-(1-piperidinyl)propoxy]phenyl}pyrido[3,4-d]pyrimidin-4(3H)-one, 6-methoxy-2-methyl-3-{4-[3-(1-pyrrolidinyl)propoxy]phenyl}pyrido[3,4-d]pyrimidin-4(3H)-one, 2,5-dimethyl-3-{4-[3-(1-pyrrolidinyl)propoxy]phenyl}-4(3H)-quinazolinone, 2-methyl-3-{4-[3-(1-pyrrolidinyl)propoxy]phenyl}-5-trifluoromethyl-4(3H)-quinazolinone, 5-fluoro-2-methyl-3-{4-[3-(1-piperidinyl)propoxy]phenyl}-4(3H)-quinazolinone, 6-methoxy-2-methyl-3-{4-[3-(1-piperidinyl)propoxy]phenyl}-4(3H)-quinazolinone, 5-methoxy-2-methyl-3-(4-{3-[(3S)-3-methylpiperidin-1-yl]propoxy}phenyl)-4(3H)-quinazolinone, 7-methoxy-2-methyl-3-(4-{3-[(3S)-3-methylpiperidin-1-yl]propoxy}phenyl)-4(3H)-quinazolinone, 2-methyl-3-(4-{3-[(3S)-3-methylpiperidin-1-yl]propoxy}phenyl)pyrido[2,3-d]pyrimidin-4(3H)-one, 5-fluoro-2-methyl-3-(4-{3-[(2R)-2-methylpyrrolidin-1-yl]propoxy}phenyl)-4(3H)-quinazolinone, 2-methyl-3-(4-{3-[(2R)-2-methylpyrrolidin-1-yl]propoxy}phenyl)pyrido[4,3-d]pyrimidin-4(3H)-one, 6-methoxy-2-methyl-3-(4-{3-[(2R)-2-methylpyrrolidin-1-yl]propoxy}phenyl)-4(3H)-quinazolinone, 6-methoxy-2-methyl-3-(4-{3-[(2S)-2-methylpyrrolidin-1-yl]propoxy}phenyl)-4(3H)-quinazolinone, and pharmaceutically acceptable salts thereof.

Specific CCK1R agonists of use in combination with a compound of the present invention include: 3-(4-{[1-(3-ethoxyphenyl)-2-(4-methylphenyl)-1H-imidazol-4-yl]carbonyl}-1-piperazinyl)-1-naphthoic acid; 3-(4-{[1-(3-ethoxyphenyl)-2-(2-fluoro-4-methylphenyl)-1H-imidazol-4-yl]carbonyl}-1-piperazinyl)-1-naphthoic acid; 3-(4-{[1-(3-ethoxyphenyl)-2-(4-fluorophenyl)-1H-imidazol-4-yl]carbonyl}-1-piperazinyl)-1-naphthoic acid; 3-(4-{[1-(3-ethoxyphenyl)-2-(2,4-difluorophenyl)-1H-imidazol-4-yl]carbonyl}-1-piperazinyl)-1-naphthoic acid; and 3-(4-{[1-(2,3-dihydro-1,4-benzodioxin-6-yl)-2-(4-fluorophenyl)-1H-imidazol-4-yl]carbonyl}-1-piperazinyl)-1-naphthoic acid; and pharmaceutically acceptable salts thereof.

Specific MC4R agonists of use in combination with a compound of the present invention include: 1) (5S)-1'-{[(3R,4R)-1-tert-butyl-3-(2,3,4-trifluorophenyl)piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 2) (5R)-1'-{[(3R,4R)-1-tert-butyl-3-(2,3,4-trifluorophenyl)-piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 3) 2-(1'-{[(3S,4R)-1-tert-butyl-4-(2,4-difluorophenyl)pyrrolidin-3-yl]carbonyl}-3-chloro-2-methyl-5H-spiro[furo[3,4-b]pyridine-7,4'-piperidin]-5-yl)-2-methylpropanenitrile; 4) 1'-{[(3S,4R)-1-tert-butyl-4-(2,4-difluorophenyl)pyrrolidin-3-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 5) N-(3R,4R)-3-({3-chloro-2-methyl-5-[1-methyl-1-(1-methyl-1H-1,2,4-triazol-5-yl)ethyl]-1'H,5H-spiro[furo-[3,4-b]pyridine-7,4'-piperidin]-1'-yl}carbonyl)-4-(2,4-difluorophenyl)-cyclopentyl]-N-methyltetrahydro-2H-pyran-4-amine; 6) 2-[3-chloro-1'-({(1R,2R)-2-(2,4-difluorophenyl)-4-[methyl(tetrahydro-2H-pyran-4-yl)amino]-cyclopentyl}-carbonyl)-2-methyl-5H-spiro[furo[3,4-b]pyridine-7,4'-piperidin]-5-yl]-2-methyl-propane-nitrile; and pharmaceutically acceptable salts thereof.

"Obesity" is a condition in which there is an excess of body fat. The operational definition of obesity is based on the Body Mass Index (BMI), calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk for obesity" is an otherwise healthy subject with a BMI of 25 kg/m$^2$ to less than 30 kg/m$^2$ or a subject with at least one co-morbidity with a BMI of 25 kg/m$^2$ to less than 27 kg/m$^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity that requires weight reduction or that would be improved by weight reduction, has a BMI greater than or equal to 25 kg/m$^2$. In Asian countries, including Japan, an "obese subject" refers to a subject with at least one obesity-induced or obesity-related co-morbidity that requires weight reduction or that would be improved by weight reduction, with a BMI greater than or equal to 25 kg/m$^2$. In Asian countries, a "subject at risk of obesity" is a subject with a BMI of greater than 23 kg/m$^2$ to less than 25 kg/m$^2$.

As used herein, the term "obesity" is meant to encompass all of the above definitions of obesity.

Obesity-induced or obesity-related co-morbidities include, but are not limited to, diabetes, non-insulin dependent diabetes mellitus-type 2, impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

"Treatment" (of obesity and obesity-related disorders) refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization, of the metabolic resistance that normally results from weight loss.

"Prevention" (of obesity and obesity-related disorders) refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The compounds of formula I are also useful for treating or preventing obesity and obesity-related disorders in cats and dogs. As such, the term "mammal" includes companion animals such as cats and dogs.

The term "diabetes," as used herein, includes both insulin-dependent diabetes mellitus (IDDM, also known as type I diabetes) and non-insulin-dependent diabetes mellitus (NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compounds of the present invention are useful for treating both Type I and Type H diabetes. The compounds are especially effective for treating Type II diabetes. The compounds of the present invention are also useful for treating and/or preventing gestational diabetes mellitus.

It will be appreciated that for the treatment or prevention of migraine, a compound of the present invention may be used in conjunction with other anti-migraine agents, such as ergotamines or 5-HT$_1$ agonists, especially sumatriptan, naratriptan, zolmatriptan or rizatriptan.

It will be appreciated that for the treatment of depression or anxiety, a compound of the present invention may be used in conjunction with other anti-depressant or anti-anxiety agents.

Suitable classes of anti-depressant agents include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine, imipramine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, 94/13644, 94/13661, 94/13676 and 94/13677. Still further, neurokinin-1 (NK-1) receptor antagonists may be favorably employed with the CB1 receptor modulators of the present invention. NK-1 receptor antagonists of use in the present invention are fully described in the art. Specific neurokinin-1 receptor antagonists of use in the present invention include: (±)-(2R3R,2 S3S)-N-{[2-cyclopropoxy-5-(trifluoromethoxy)-phenyl]methyl}-2-phenylpiperidin-3-amine; 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl) morpholine; aperpitant; CJ17493; GW597599; GW679769; R673; R067319; R1124; R1204; SSR146977; SSR240600; T-2328; and T2763; or a pharmaceutically acceptable salts thereof.

Suitable atypical anti-depressants include: bupropion, lithium, nefazodone, trazodone and viloxazine, and pharmaceutically acceptable salts thereof.

Suitable classes of anti-anxiety agents include benzodiazepines and $5\text{-}HT_{1A}$ agonists or antagonists, especially $5\text{-}HT_{1A}$ partial agonists, and corticotropin releasing factor (CRF) antagonists. Suitable benzodiazepines include: alprazolam, chlordiazepoxide, clonazepam, chlorazepate, diazepam, halazepam, lorazepam, oxazepam and prazepam, and pharmaceutically acceptable salts thereof. Suitable $5\text{-}HT_{1A}$ receptor agonists or antagonists include, in particular, the $5\text{-}HT_{1A}$ receptor partial agonists buspirone, flesinoxan, gepirone and ipsapirone, and pharmaceutically acceptable salts thereof. Suitable corticotropin releasing factor (CRF) antagonists include those previously discussed herein.

It will be appreciated that a combination of a conventional antipsychotic drug with a $5\text{-}HT_6$ receptor modulator may provide an enhanced effect in the treatment of mania. Such a combination would be expected to provide for a rapid onset of action to treat a manic episode thereby enabling prescription on an "as needed basis". Furthermore, such a combination may enable a lower dose of the antipsychotic agent to be used without compromising the efficacy of the antipsychotic agent, thereby minimizing the risk of adverse side-effects. A yet further advantage of such a combination is that, due to the action of the $5\text{-}HT_6$ receptor modulator, adverse side-effects caused by the antipsychotic agent such as acute dystonias, dyskinesias, akathesia and tremor may be reduced or prevented.

Thus, according to a further aspect of the present invention there is provided the use of a $5\text{-}HT_6$ receptor modulator and an antipsychotic agent for the manufacture of a medicament for the treatment or prevention of mania.

The present invention also provides a method for the treatment or prevention of mania, which method comprises administration to a patient in need of such treatment or at risk of developing mania of an amount of a $5\text{-}HT_6$ receptor modulator and an amount of an antipsychotic agent, such that together they give effective relief.

In a further aspect of the present invention, there is provided a pharmaceutical composition comprising a $5\text{-}HT_6$ receptor modulator and an antipsychotic agent, together with at least one pharmaceutically acceptable carrier or excipient, wherein the $5\text{-}HT_6$ receptor modulator and the antipsychotic agent may be present as a combined preparation for simultaneous, separate or sequential use for the treatment or prevention of mania. Such combined preparations may be, for example, in the form of a twin pack.

In a further or alternative aspect of the present invention, there is therefore provided a product comprising a $5\text{-}HT_6$ receptor modulator and an antipsychotic agent as a combined preparation for simultaneous, separate or sequential use in the treatment or prevention of mania.

It will be appreciated that when using a combination of the present invention, the $5\text{-}HT_6$ receptor modulator and the antipsychotic agent may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, the antipsychotic agent may be administered as a tablet and then, within a reasonable period of time, the $5\text{-}HT_6$ receptor modulator may be administered either as an oral dosage form such as a tablet or a fast-dissolving oral dosage form. By a "fast-dissolving oral formulation" is meant, an oral delivery form which when placed on the tongue of a patient, dissolves within about 10 seconds.

Included within the scope of the present invention is the use of $5\text{-}HT_6$ receptor modulators in combination with an antipsychotic agent in the treatment or prevention of hypomania.

It will be appreciated that a combination of a conventional antipsychotic drug with a $5\text{-}HT_6$ receptor modulator may provide an enhanced effect in the treatment of schizophrenic disorders. Such a combination would be expected to provide for a rapid onset of action to treat schizophrenic symptoms thereby enabling prescription on an "as needed basis".

As used herein, the term "schizophrenic disorders" includes paranoid, disorganized, catatonic, undifferentiated and residual schizophrenia; schizophreniform disorder; schizoaffective disorder; delusional disorder; brief psychotic disorder; shared psychotic disorder; substance-induced psychotic disorder; and psychotic disorder not otherwise specified.

Other conditions commonly associated with schizophrenic disorders include self-injurious behavior (e.g. Lesch-Nyhan syndrome) and suicidal gestures.

Suitable antipsychotic agents of use in combination with a 5-$HT_6$ receptor modulator include the phenothiazine, thioxanthene, heterocyclic dibenzazepine, butyrophenone, diphenylbutylpiperidine and indolone classes of antipsychotic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. Suitable examples of dibenzazepines include clozapine and olanzapine. An example of a butyrophenone is haloperidol. An example of a diphenylbutylpiperidine is pimozide. An example of an indolone is molindolone. Other antipsychotic agents include loxapine, sulpiride and risperidone. It will be appreciated that the antipsychotic agents when used in combination with a 5-$HT_6$ receptor modulator may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, olanzapine, haloperidol, pimozide and risperidone are commonly used in a non-salt form.

Other classes of antipsychotic agent of use in combination with a 5-$HT_6$ receptor modulator include dopamine receptor antagonists, especially D2, D3 and D4 dopamine receptor antagonists, and muscarinic m1 receptor agonists. An example of a D3 dopamine receptor antagonist is the compound PNU-99194A. An example of a D4 dopamine receptor antagonist is PNU-101387. An example of a muscarinic m1 receptor agonist is xanomeline.

Another class of antipsychotic agent of use in combination with a 5-$HT_6$ receptor modulator is the 5-$HT_{2A}$ receptor antagonists, examples of which include MDL100907 and fananserin. Also of use in combination with a 5-$HT_6$ receptor modulator are the serotonin dopamine antagonists (SDAs) which are believed to combine 5-$HT_{2A}$ and dopamine receptor antagonist activity, examples of which include olanzapine and ziperasidone.

Still further, NK-1 receptor antagonists may be favorably employed with the 5-$HT_6$ receptor modulators of the present invention. Preferred NK-1 receptor antagonists for use in the present invention are selected from the classes of compounds described previously.

The present invention also provides a method for the treatment or prevention of epilepsy, which method comprises administration to a patient in need of such treatment an amount of a compound of the present invention and an amount of an anti-epileptic agent, such that together they give effective relief.

The present invention also provides a method for the treatment or prevention of Alzheimer's Disease, which method comprises administration to a patient in need of such treatment an amount of a compound of the present invention and an amount of an anti-Alzheimer's Disease agent, such that together they give effective relief.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs and cats.

The weight ratio of the compound of the Formula I to the second active ingredient may be varied and will depend upon the effective dose of each ingredient. Generally, an effective dose of each will be used. Thus, for example, when a compound of the Formula I is combined with a β-3 agonist the weight ratio of the compound of the Formula I to the β-3 agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

The following abbreviations are used in the schemes and examples of the present invention: RBF is round bottom flask; DMF is dimethyl formamide; MPLC is medium pressure liquid chromatography; HPLC is high pressure liquid chromatography; L is liter; mmol is millimole; mol is mole; g is gram; mg is milligram; ml or mL is milliliter; hr or h is hour(s); N is normal; h is hour(s); min is minute(s); Me is methyl; MeOH is methanol; BOC or Boc is tert-butoxy; EtOAc is ethyl acetate; M is molar; Tos or Ts is toluene sulfonyl, TsCl or TosCl is toluene sulfonyl chloride; and THF is tetrahydrofuran.

The following reaction schemes illustrate methods which may be employed for the synthesis of the novel tryptamine sulfonamides of structural formula I described in this invention. All substituents are as defined above unless indicated otherwise. Several strategies based upon synthetic transformations known in the literature of organic synthesis may be employed for the preparation of the title compounds of general formula I. A preferred synthetic process to make compounds of general formula I wherein X is oxygen or sulfur and R1 is hydrogen is shown in the General Synthetic Scheme below.

General Synthetic Scheme

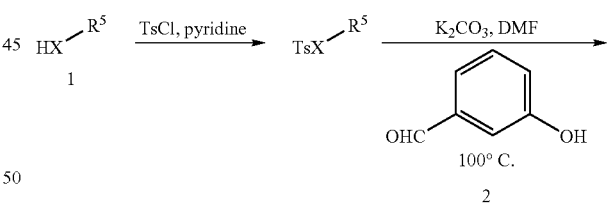

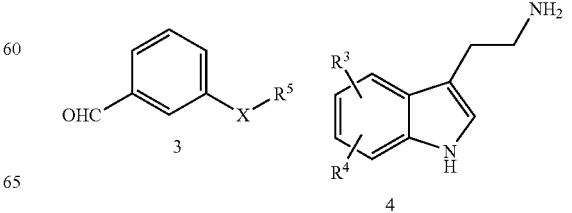

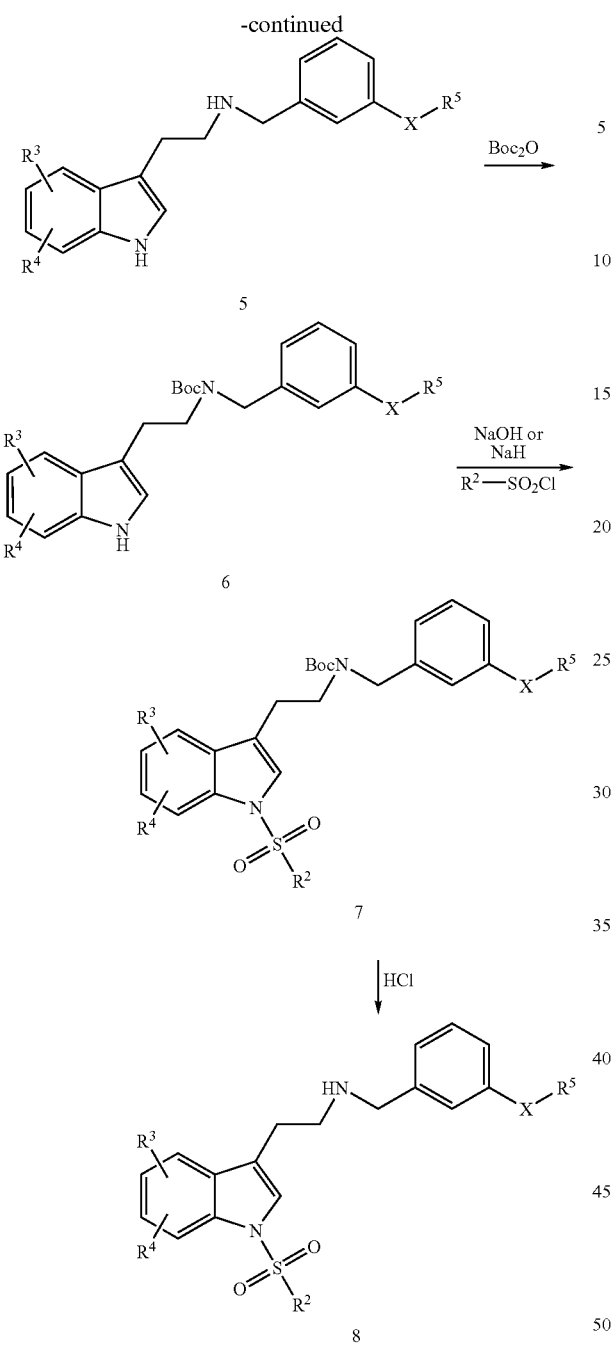

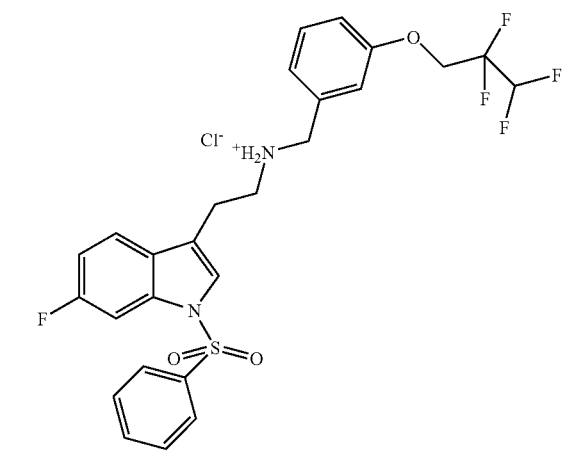

lowed by reduction with NaBH$_4$ or NaBH$_3$CN. The resulting amines 5 can be protected in a number of ways including as their Boc-carbamates (using Boc$_2$O) to give compounds 6. The indole sulfonamides 7 can be prepared by reaction of 6 with a sulfonyl chloride (R$^2$—SO$_2$Cl) in the presence of a base (such as NaOH or NaH). Then target compounds 8 can be prepared by removal of the protective group. For example, compounds 7 can be treated with HCl in dioxane, ether, or ethyl acetate to give 8.

In order to illustrate the invention, the following examples are included. These examples do not limit the invention. They are only meant to suggest a method of reducing the invention to practice. Those skilled in the art may find other methods of practicing the invention which are readily apparent to them. However, those methods are also deemed to be within the scope of this invention.

EXAMPLE 1

Step A: Into a 1 L 3-necked RBF fitted with a thermometer/N$_2$ inlet and magnetically stirred was added 2,2,3,3-tetrafluoropropyl p-toluenesulfonate (Matrix #003479 lot #V16E, 25 g, 87 mmol), 3-hydroxybenzaldehyde (Aldrich #H1,980-8 lot #10420CS, 12.8 g, 105 mmol), potassium carbonate (Sigma/Aldrich #347825 lot #10106CE, 18.1 g, 131 mmol), and DMF (200 mL). The mixture was heated at 100° C. via heating mantle for 16 hours. The reaction mixture was then cooled to room temperature, and poured into a separatory funnel containing 2 L of ice water. The mixture was extracted 3 times with ethyl acetate, and the organic extracts were combined and washed twice with 1N NaOH, once with saturated NaHCO$_3$ and once with brine. The organic layer was dried over MgSO$_4$, filtered, and concentrated under vacuum to give a dark oil. The oil was purified by MPLC on a 330 g Redi Sep silica gel cartridge flushed with 25% CH$_2$Cl$_2$/heptane; and eluted with: 600 mL of 25% CH$_2$Cl$_2$/heptane, 1 L 40% CH$_2$Cl$_2$/heptane, and 2 L 50% CH$_2$Cl$_2$/heptane to give 2,2,3,3-tetrafluoropropylbenzaldehyde as a yellow oil.

Step B: 6-Fluorotryptamine (MP Biomedicals #158153 lot 1126J and Sigma #F-7126 lot 129H0746 for a total of 6.18 g, 34 mmol) was dissolved in approximately 125 mL of isopropanol. To this mixture was added 2,2,3,3-tetrafluoropropylbenzaldehyde from Step A (7.2 g, 30.5 mmol). The resulting mixture was heated at reflux using a heating mantle under N$_2$ using a heating mantle for 4.5 hours. Then the reaction mixture was allowed to cool to room temperature, and allowed to sit overnight. The reaction mixture was then re-heated to 50° C. and sodium borohydride (Sigma/

Alcohols or thiols such as 1 can be converted to their corresponding tosylates (or mesylates) by treatment with the appropriate sulfonyl chloride (like TosCl) in the presence of a base (such as pyridine). Alternatively, R$^5$=Br or R$^5$=I can be used as electrophiles in the following step. The resulting tosylates (or mesylates, bromides, and iodides) can then be reacted with hydroxybenzaldehyde 2 (or the related thiophenols) in the presence of a base (such as potassium carbonate) and using several possible solvents including DMF and THF to give the ethers (or sulfides) 3. The reaction may proceed at various temperatures (for example 100° C.) depending on the substrates. Reductive amination of 3 can easily be achieved with tryptamine or substituted tryptamine 4. This can be accomplished in a number of ways, including by a two step process involving formation of the corresponding imine, fol- Aldrich #213462 lot 03826LD, 1.21 g, 32 mmol) was added in one portion. The mixture was stirred for 2 hours, then water was carefully added and the reaction mixture was allowed to cool to room temperature. The reaction mixture was concentrated under reduced pressure to remove the isopropanol. The residue was transferred to a separatory funnel and extracted three times with CH$_2$Cl$_2$. The organic layers were combined and approximately 40 mL 1 N HCl was added. The mixture was stirred at room temperature for approximately 1.5 hours, then filtered, washed with water, and partially dried. The collected solids were triturated with ether, then heptane, and then air dried in a funnel to give the product, N-(2-(6-Fluoro-1H-indole-3-yl)ethyl)-3-(2,2,3,3-tetrafluoropropyl)benzylamine, as an off white solid. The filtrate was re-filtered to obtain additional product. The aqueous layers were then combined and made basic with saturated NaHCO$_3$ solution. The basified aqueous solution was then extracted three times with CH$_2$Cl$_2$, dried over MgSO$_4$, filtered, and concentrated to give an oil. The oil was dissolved in CH$_2$Cl$_2$ and purified by MPLC on 90 g silica gel cartridge equilibrated with 2% MeOH/CH$_2$Cl$_2$ by eluting with 2%-5% MeOH/CH$_2$Cl$_2$ to afford an additional N-(2-(6-Fluoro-1H-indole-3-yl)ethyl)-3-(2,2,3,3-tetrafluoropropyl)benzylamine.

Step C: N-(2-(6-Fluoro-1H-indole-3-yl)ethyl)-3-(2,2,3,3-tetrafluoropropyl)benzylamine (12.0 g, 30.1 mmol) was added to a 1 L RBF fitted with an N$_2$ inlet and magnetic stirring. CH$_2$Cl$_2$ was added and the resulting suspension was stirred while adding triethylamine (Aldrich #47, 128-3 lot JO10526DO, 4.57 g, 45.2 mmol). To the resulting solution was added di-tert-butyl-dicarbonate (Acros #189775000 lot AO214831001, 7.23 g, 33.1 mmol), and the mixture was stirred at room temperature for 1 hour. The reaction mixture was poured into separatory funnel containing brine. The layers were separated and the aqueous layer was extracted twice more with CH$_2$Cl$_2$, and then dried over MgSO$_4$, filtered, and concentrated to give crude product. The crude product was dissolved in CH$_2$Cl$_2$ and purified by MPLC on 120 g silica gel cartridge flushed with 20% ethyl acetate/heptane by eluting with 20% ethyl acetate/heptane-40% ethyl acetate/heptane to afford the Boc indole as a thick oil.

Step D: Into a 500 mL 3 neck RBF fitted with a thermometer/N$_2$ inlet, addition funnel and magnetic stirring was added 100 mL DMF, which was cooled to about 0° C. using an ice bath. Sodium hydride 60% (Aldrich #452912-100 g lot 10429PD, 1.38 g, 34.2 mmol) was added and the mixture was allowed to stir until the foaming subsided. To this mixture was added a solution of the BOC indole from Step C (15.5 g, 31.1 mmol) in 50 mL DMF via an addition funnel. When the resulting reaction mixture had cooled back down, benzenesulfonyl chloride (Acros #14847 2500 lot AO16623101, 6.59 g, 37.3 mmol) was added dropwise via pipette. After 10 minutes, the ice bath was removed and the mixture was allowed to warm to room temperature under N$_2$. The reaction mixture was stirred overnight, then poured into 1.5 L of ice water. After transferring to a separatory funnel, the mixture was extracted three times with ether. The combined extracts were washed with brine, dried over MgSO$_4$, filtered, and concentrated to give a thick oil. The oil was dissolved in a minimum volume of CH$_2$Cl$_2$ and diluted with heptane, and then purified by MPLC on 330 g silica gel cartridge pretreated with 10% EtOAc/Heptane, by eluting with 10%, 15%, 20%, 25% and 30% ethyl acetate/heptane to afford the BOC indole sulfonamide product.

Step E: The BOC indole sulfonamide from Step D (14.7 g, 32.0 mmol) was dissolved in 50 mL of ether. To this mixture was added 100 mL hydrogen chloride (100 mmol/4.34 equivalents, 1 M solution in diethyl ether (Aldrich #294837-800 ml lot 11628EC). The mixture was stirred at room temperature under N$_2$ overnight. The mixture was then concentrated on a rotary evaporator and the residue was dissolved in 100 mL hydrogen chloride (400 mmol/17.4 equivalents, 4 M solution in 1,4-dioxane (Aldrich #345547-800 ml lot 08711CC) and stirred at room temperature under N$_2$ for about 1 hour. The reaction mixture was concentrated to a thick oil. The oil was dissolved in a minimum volume of dioxane and diluted with toluene, then concentrated to give a solid. Ether was added and the mixture was stirred magnetically. The mixture was then filtered, washed well with ether, and air dried to give the crude desired product as a white solid. $^1$H NMR (500 MHz, CDCl$_3$) of Example 1 as the hydrochloride salt: $^1$H NMR (500 MHz, d6-DMSO): δ 9.53 (br s, 2H), 8.03 (d, J=7.5 Hz, 2H), 7.79 (s, 1H), 7.72 (m, 3H), 7.61 (t, J=7.5 Hz, 2H), 7.40 (t, J=8 Hz, 1H), 7.36 (br s, 1H), 7.18-7.23 (m, 2H), 7.12 (dd, J=8.5, 2.5 Hz, 1H), 6.70 (tt, J=52.0, 5.5 Hz, 1H), 4.62 (t, J=13.5 Hz, 2H), 4.15 (s, 2H), 3.19 (m, 2H), 3.12 (m, 2H).

The crude product may be purified by HPLC. Salts of Example 1 may be prepared following purification by HPLC. The TFA salt of Example 1 is obtained directly after lyophilization. Alternatively, the freebase of Example 1 can be dissolved in acetic acid and lyophilized to give the acetic acid salt of Example 1. The free base of Example 1 may also be treated with one equivalent of HCl to provide the mono HCl salt of Example 1. HPLC/MS for the acetic acid salt of Example 1: (M+1)=539.2. HPLC/MS for the trifluoroacetic acid salt of Example 1 (M+1)=539.23.

Using the general procedure described in Example 1, and the appropriate starting material the following compounds were obtained:

| | Structure | HPLC/MS m/z (M + 1) |
|---|---|---|
| Example 2 L-001426817-001F | 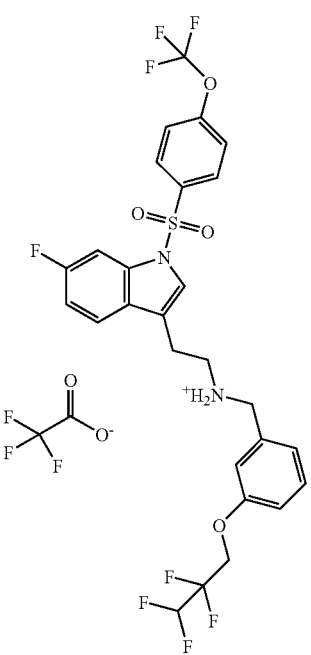 | 623.1 |

| | Structure | HPLC/MS m/z (M+1) |
|---|---|---|
| Example 3 L-001426818-001P | 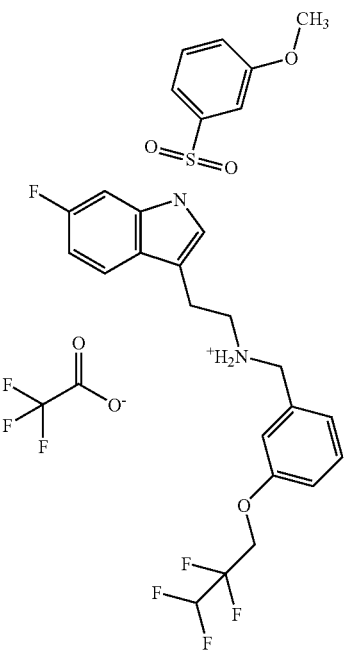 | 569.2 |
| Example 4 L-001426819-001Y | 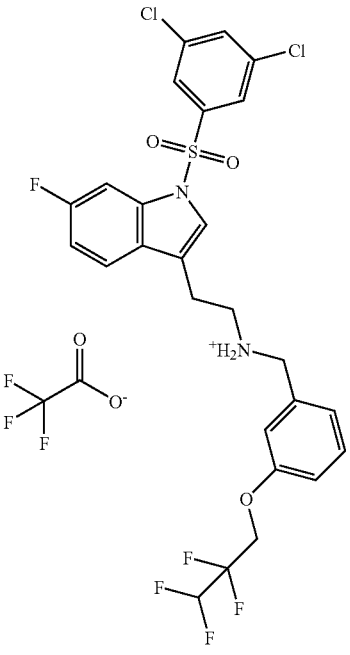 | 573.1, 575.1 |
| Example 5 L-001426820-001M | 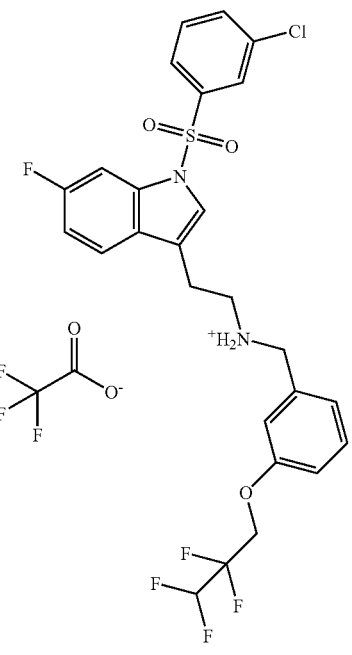 | 607.1, 609.1 |
| Example 6 L-001426821-001W | 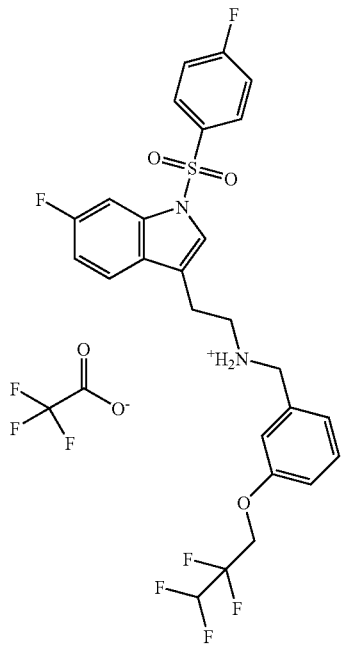 | 557.2 |

-continued
| Structure | HPLC / MS m/z (M + 1) |
|---|---|
| Example 7 L-001426822-001E 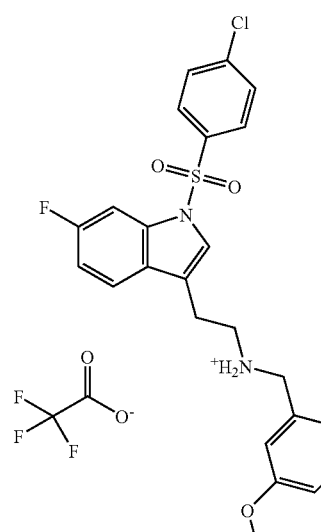 | 573.1 |
| Example 8 L-001426823-001N | 617.1, 619.0 |
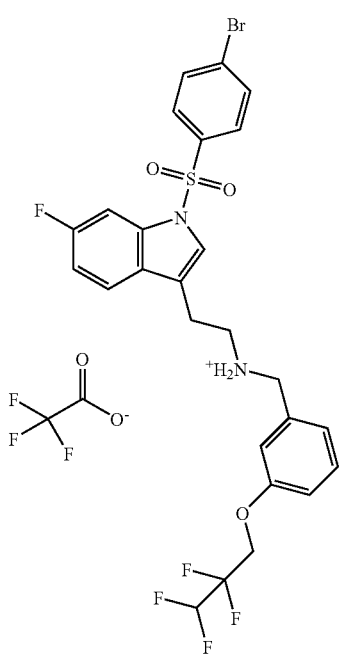
-continued
| Structure | HPLC / MS m/z (M + 1) |
|---|---|
| Example 9 L-001426824-001X | 591.1, 593.1 |
| Example 10 L-001426825-001F | 607.2 |
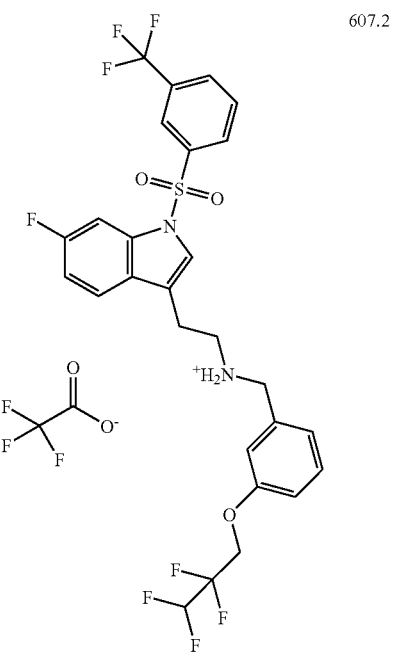

| | Structure | HPLC/MS m/z (M+1) |
|---|---|---|
| Example 11 L-001426826-001P | 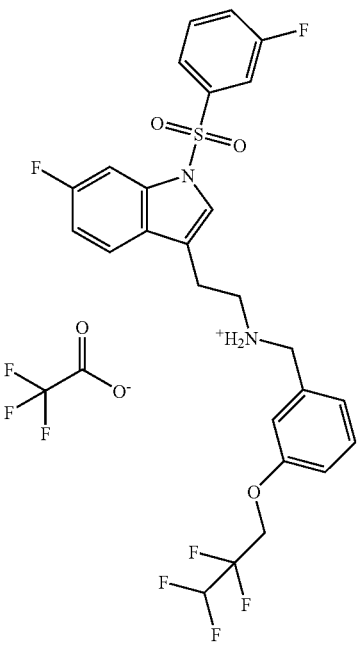 | 557.2 |
| Example 12 L-001426828-001G | 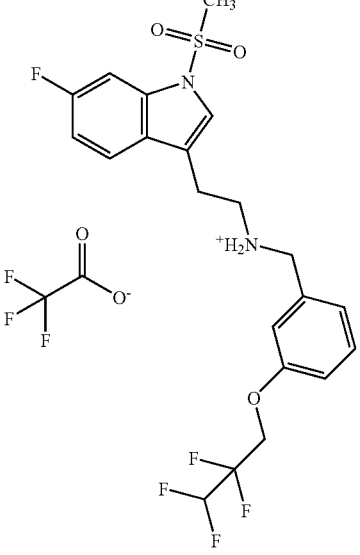 | 477.2 |
| | Structure | HPLC/MS m/z (M+1) |
|---|---|---|
| Example 13 L-001426829-001R | 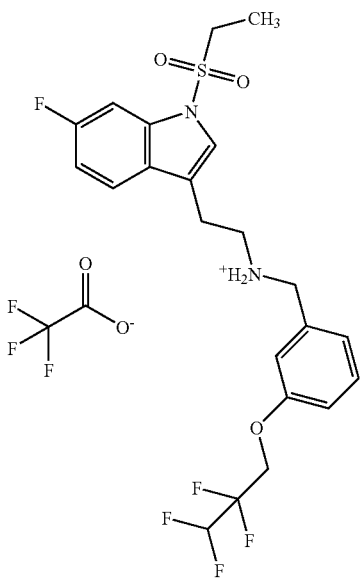 | 491.2 |
| Example 14 L-001426830-001E | 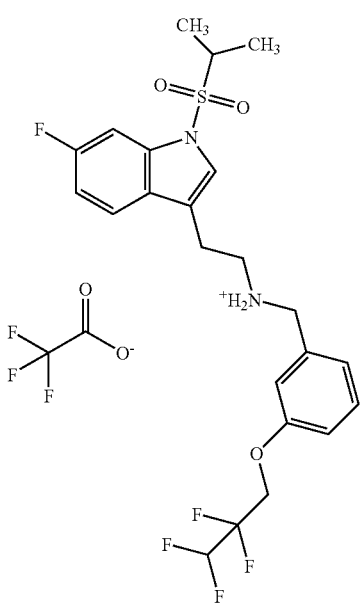 | 505.2 |

| Structure | HPLC / MS m/z (M + 1) |
|---|---|
| Example 15 L-001426831-001N | 569.3 |

BIOLOGICAL EXAMPLE 1

5-HT$_6$ Receptor Binding Assay

Affinity (IC$_{50}$) of a compound for cloned human, rat, or mouse 5-HT$_6$ receptor was measured by its ability to displace [$^3$H]5-HT using cell membranes prepared from cultured cells and scintillation proximity assay (SPA) beads that bind to cell membranes (Catalog No. RPNQ0001; GE Healthcare Life Sciences, Piscataway, N.J.). Assays were carried out in 200 μl binding buffer (50 mM Tris-HCl, pH 7.4, 5 mM MgCl$_2$, 0.5 mM EDTA, 10 μM pargyline and 0.1% ascorbic acid) in 96-well plates. Cell membranes were re-suspended in binding buffer to final concentration of up to 0.2 mg protein/ml and mixed with reconstituted SPA beads to a final concentration of 0.25 mg/ml. To each well, 145 μl of above mixture, 50 of cold compound (to 10$^{-10}$ to 10$^{-5}$ M final concentration) and 50 μl of [$^3$H]5-HT radioligand (specific activity, 100 Ci/mmol, GE Healthcare Life Sciences; final concentration, 5 nM) were added. Following 1 h incubation at room temperature, the radioactivity bound to the cell membranes was measured on a scintillation counter.

The compounds of the present invention have IC$_{50}$ values of less than 5 micromolar in the 5-HT$_6$ binding assay. In particular, compounds of Examples 1 to 15 were assayed in the 5-HT$_6$ binding assay and found to have IC$_{50}$ values for the human 5-HT$_6$ receptor less than 5 micromolar. Specific IC$_{50}$ values for the compounds of the present invention are shown in Table 2.

TABLE 2

5-HT$_6$ Receptor Binding Activity for Selected Compounds

| Example No. | Mouse 5-HT$_6$ binding IC$_{50}$ (nM) | Human 5-HT$_6$ binding IC$_{50}$ (nM) |
|---|---|---|
| 1 | 2 | 0.2 |
| 2 | 210.6 | 46.36 |
| 3 | 170.4 | 0.5932 |
| 4 | 60.23 | 0.8054 |
| 5 | 148.2 | 2.885 |
| 6 | 21.55 | 2.885 |
| 7 | 7.266 | 3.398 |
| 8 | 15.43 | 2.05 |
| 9 | 126.7 | 8.85 |
| 10 | 60.03 | 0.626 |
| 11 | 17.59 | 0.3707 |
| 12 | 9.508 | 1.606 |
| 13 | 11.7 | 2.615 |
| 14 | 57.1 | 20 |
| 15 | 187.5 | 10.18 |

BIOLOGICAL EXAMPLE 2

5-HT$_6$ Receptor Functional Activity Assay.

The functional activation of human, rat, or mouse 5-HT$_6$ receptor expressed in CHO cells was determined by measuring cellular cAMP levels following the exposure of the cells to a compound using the SPA cAMP Screening System (Catalog No. RPA556, GE Healthcare) in 96-well OptiPlates (Catalog No. 6005190, PerkinElmer, Boston, Mass.). Cells expressing recombinant receptors were harvested and then re-suspended at approximately 2.0×10$^6$ cells/ml in assay medium containing Earle's Balanced Salt Solution (EBSS, pH 7.4) supplemented with 25 mM Hepes, 5 mM MgCl$_2$ and 0.05% BSA. Cells (50 μl, ~10$^5$ cells) were transferred to wells, to give a final volume of 100 μl containing various concentrations of compounds. The plate was incubated at 37° C. for 30 min and the reaction was terminated by boiling for 3 min. The accumulation of cAMP in 15 μl lysate was measured according to manufacture's instructions.

The compounds of the present invention useful to treat obesity are tested at the 5-HT$_6$ receptor and are found not to show detectable activity at the 5-HT$_6$ receptor up to a 10 micromolar concentration of each compound. In particular, the compound of Example 1 did not show detectable activity at the 5-HT$_6$ receptor at a concentration up to 10 micromolar.

BIOLOGICAL EXAMPLE 3

Acute Food Intake Studies in Rats or Mice:

Adult male diet-induced obese (DIO) SD rats or C57Bl6 mice are used in these studies. The rodents are individually caged under a 12-hour light/dark cycle in a temperature- and humidity-controlled environment with free access to food and water and maintained on a fat-rich diet (rats: D12266B, 32% kcal from fat, Research Diets, New Brunswick, N.J.; mice: D12492, 60% kcal from fat, Research Diets). The Compound is administered by oral gavage using 5% Tween 80 and 0.5% methylcellulose as the vehicle approximately 30 minutes prior to the onset of the dark phase of the light cycle. Food consumption is measured at several time intervals. Overnight (16-18 hours after the onset of the dark phase of the light cycle) body weight changes are also measured.

BIOLOGICAL EXAMPLE 4

Sub-Chronic Food Intake and Body Weight Studies in Mice:

Male lean C57Bl6 mice (6-8 weeks of age) are individually caged under a 12-hour light/dark cycle and maintained on a regular chow diet (Diet 7012, Harlan Teklad, Madison, Wis.). The Compound is administered twice daily (9 AM and 5 PM) for four consecutive days by oral gavage using 5% Tween 80 and 0.5% methylcellulose as the vehicle. Upon dosing, the diet is switched to a high-fat diet (S3282, 60% kcal from fat, Bio-Serv, Frenchtown, N.J.). Daily food intake and body weight changes are measured, from which cumulative food intake and body weight changes are calculated.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of structural formula I:

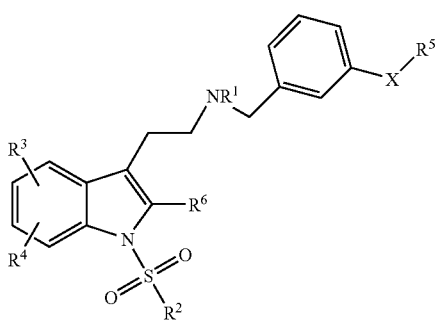

or a pharmaceutically acceptable salt thereof, wherein:
X is selected from the group consisting of:
(1) —O—,
(2) —NH—,
(3) —S—,
(4) —SO$_2$—,
(5) —CH$_2$—,
(6) —CHF—,
(7) —CF$_2$—,
(8) —CH(OH)—,
(9) —CO—,
(10) —NHCO—,
(11) —CONH—, and
(12) —CO$_2$—;

$R^1$ is selected from the group consisting of:
(1) -hydrogen, and
(2) —C$_{1-3}$alkyl;
$R^2$ is selected from the group consisting of:
(1) —C$_{1-6}$alkyl,
(2) —C$_{3-7}$cycloalkyl,
(3) —C$_{2-6}$cycloheteroalkyl,
(4) phenyl,
(5) naphthyl, and
(6) heteroaryl,
wherein each alkyl, cycloalkyl, cycloheteroalkyl, phenyl, naphthyl and heteroaryl is unsubstituted or substituted with 1, 2 or 3 substituents selected from —C$_{1-6}$alkyl, —C$_{3-7}$cycloalkyl, halogen, —CF$_3$, —OCF$_3$, —CN, —SO$_2$R$^7$, —CO$_2$R$^8$, phenyl, —C$_{2-6}$cycloheteroalkyl, —OR$^7$, —SR$^7$, —CONHR$^8$, —NHSO$_2$R$^7$, and —NHCOR$^7$;
$R^3$ and $R^4$ are each independently selected from the group consisting of:
(1) hydrogen,
(2) halogen,
(3) —C$_{1-6}$alkyl,
(4) —OC$_{1-6}$alkyl,
(5) —CN,
(6) —OR$^7$,
(7) —SO$_2$R$^7$,
(8) —SR$^7$,
(9) —N(R$^8$)$_2$,
(10) —CONHR$^8$,
(11) —NHSO$_2$R$^7$, and
(12) —NHCOR$^7$,
wherein each alkyl is unsubstituted or substituted on each carbon with 1, 2 or 3 substituents selected from halogen, —C$_{1-6}$alkyl, —C$_{3-7}$cycloalkyl, —CF$_3$, —OCF$_3$, —CN, —SO$_2$R$^7$, —CO$_2$R$^8$, phenyl, —C$_{2-6}$cycloheteroalkyl, —OR$^7$, —SR$^7$, —CONHR$^8$, —NHSO$_2$R$^7$, and —NHCOR$^7$;
$R^5$ is selected from the group consisting of:
(1) —C$_{1-6}$alkyl,
(2) —C$_{1-6}$alkenyl,
(3) phenyl, and
(4) benzyl,
wherein each alkyl, alkenyl, phenyl and benzyl is unsubstituted or substituted on each carbon with 1, 2 or 3 substituents selected from: halogen, —C$_{1-6}$alkyl, —C$_{3-7}$cycloalkyl, —CF$_3$, —OCF$_3$, —CN, —SO$_2$R$^7$, —CO$_2$R$^8$, phenyl, —C$_{2-6}$cycloheteroalkyl, —OR$^7$, —SR$^7$, —CONHR$^8$, —NHSO$_2$R$^7$, and —NHCOR$^7$;
$R^6$ is selected from the group consisting of:
(1) hydrogen, and
(2) —C$_{1-4}$alkyl;
$R^7$ is selected from the group consisting of:
(1) —C$_{1-6}$alkyl, and
(2) —C$_{3-6}$cycloalkyl; and
$R^8$ is selected from the group consisting of:
(1) hydrogen,
(2) —C$_{1-6}$alkyl, and
(3) —C$_{3-6}$cycloalkyl.

2. The compound according to claim 1, wherein $R^1$ and $R^6$ are hydrogen; or a pharmaceutically acceptable salt thereof.

3. The compound according to claim 2, wherein X is —O—; or a pharmaceutically acceptable salt thereof.

4. The compound according to claim 3, wherein $R^3$ is selected from the group consisting of:
(1) hydrogen,
(2) fluoro,
(3) chloro, (4) bromo,
(5) —CF$_3$,
(6) —OCF$_3$,
(7) —CN,
(8) —OR$^7$,
(9) —SO$_2$R$^7$, and
(10) —SR$^7$;
or a pharmaceutically acceptable salt thereof.

5. The compound according to claim 4, wherein R$^4$ is selected from the group consisting of:
(1) hydrogen,
(2) fluoro, and
(3) chloro;
or a pharmaceutically acceptable salt thereof.

6. The compound according to claim 5, wherein R$^3$ is fluoro and R$^4$ is hydrogen; or a pharmaceutically acceptable salt thereof.

7. The compound according to claim 1, wherein R$^2$ is selected from:
(1) methyl,
(2) ethyl,
(3) isopropyl, and
(4) phenyl,
wherein phenyl is unsubstituted or substituted with 1, 2 or 3 substituents selected from halogen, CF$_3$, OCF$_3$ and —OCH$_3$; or a pharmaceutically acceptable salt thereof.

8. The compound according to claim 1, wherein R$^5$ is C$_{2-4}$ alkyl, wherein each alkyl carbon is unsubstituted or substituted with 1, 2 or 3 fluoro substituents; or a pharmaceutically acceptable salt thereof.

9. The compound according to claim 1, wherein R$^5$ is —CH$_2$CF$_2$CHF$_2$; or a pharmaceutically acceptable salt thereof.

10. The compound according to claim 1 of structural formula IC:

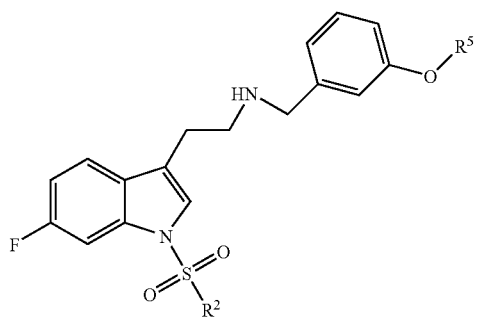

IC or a pharmaceutically acceptable salt thereof, wherein:
R$^2$ is selected from:
(1) methyl,
(2) ethyl,
(3) isopropyl, and
(4) phenyl,
wherein phenyl is unsubstituted or substituted with 1, 2 or 3 substituents selected from halogen, CF$_3$, OCF$_3$ and —OCH$_3$; and
R$^5$ is C$_{2-4}$ alkyl, wherein each alkyl carbon is unsubstituted or substituted with 1, 2 or 3 fluoro substituents.

11. The compound according to claim 1, selected from:

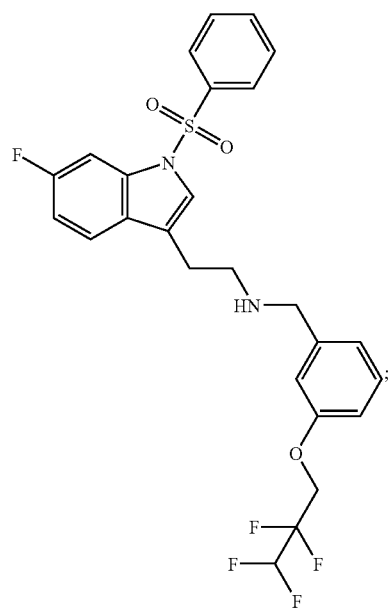

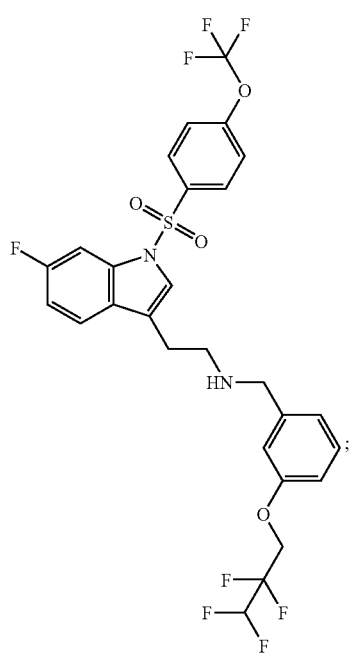

51
-continued
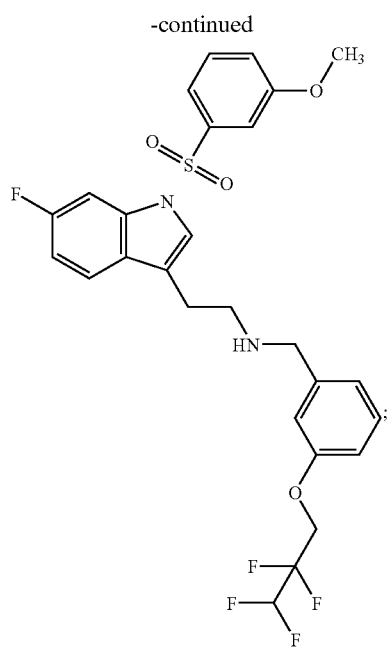
52
-continued
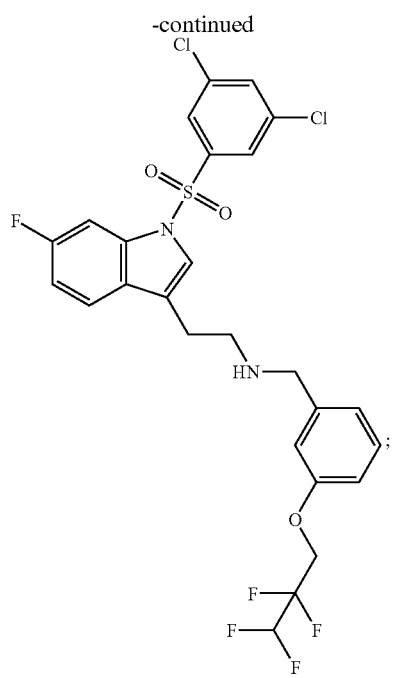
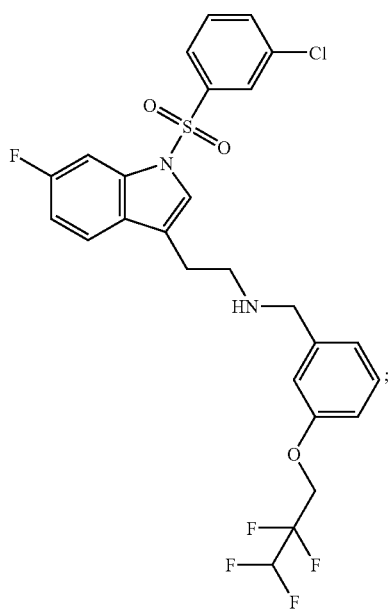

53
-continued
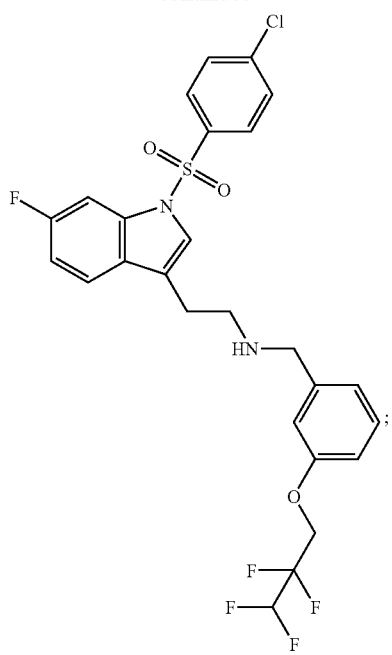
54
-continued
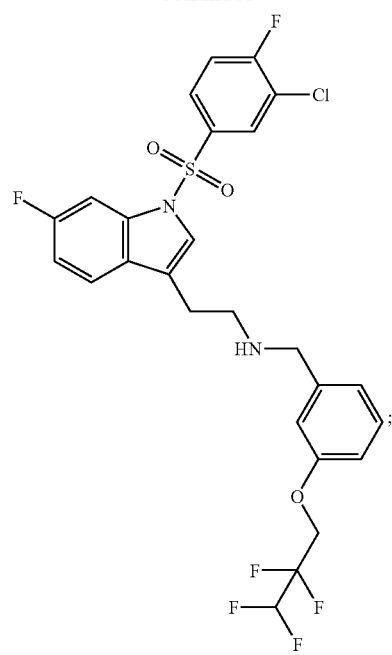
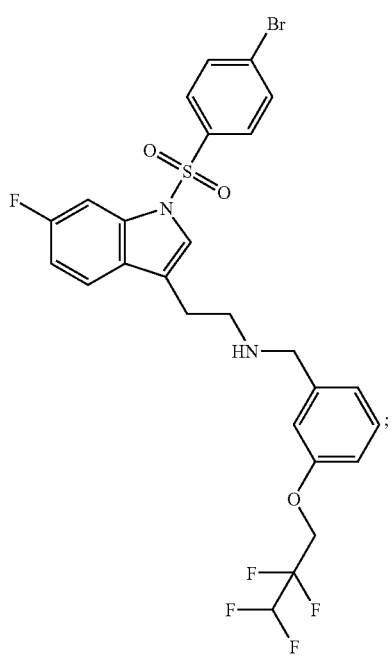
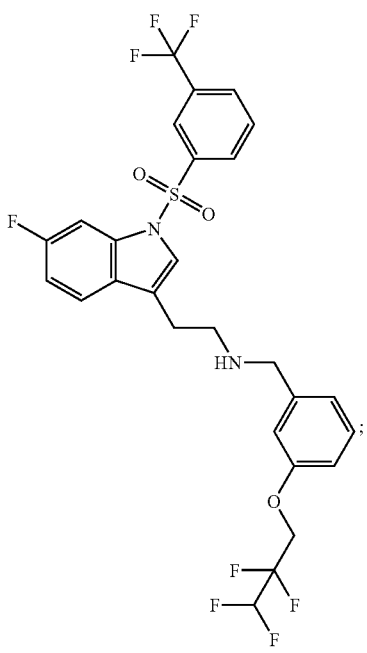

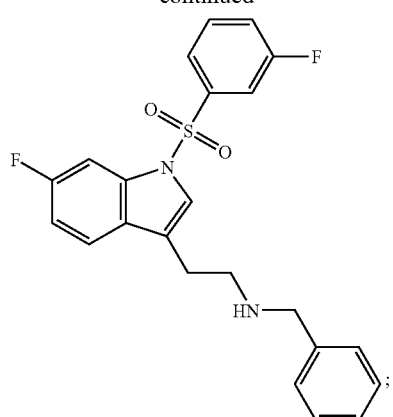
or a pharmaceutically acceptable salt thereof.

12. The compound according to claim 1, selected from:

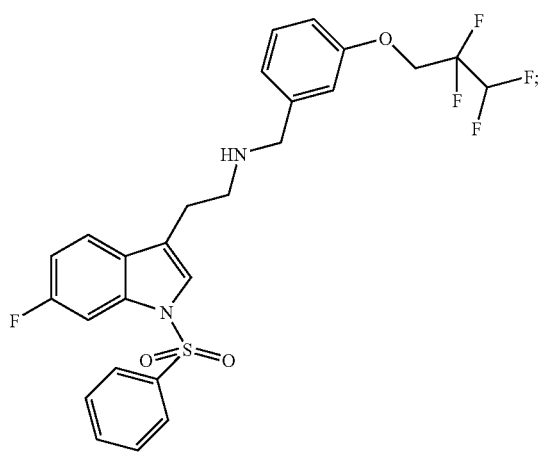

or a pharmaceutically acceptable salt thereof.

13. A composition comprising a compound according to claim 1 and a pharmaceutically acceptable carrier.

14. A composition comprising a compound according to claim 1 and a compound selected from simvastatin, taranabant, ezetimibe and sitagliptin; and a pharmaceutically acceptable carrier.

15. A method of treating obesity in a patient in need thereof comprising administration of a therapeutically effective amount of a compound according to claim 1.

* * * * *